(12) United States Patent
Mileusnic et al.

(10) Patent No.: US 7,622,446 B2
(45) Date of Patent: *Nov. 24, 2009

(54) POLYPEPTIDES, DERIVATIVES AND USES THEREOF

(75) Inventors: Radmila Mileusnic, Milton Keynes (GB); Steven Peter Russell Rose, Milton Keynes (GB)

(73) Assignee: The Open University, Milton Keynes (GB)

(*) Notice: Subject to any disclaimer, the term of this patent is extended or adjusted under 35 U.S.C. 154(b) by 215 days.

This patent is subject to a terminal disclaimer.

(21) Appl. No.: 10/475,281

(22) PCT Filed: Apr. 17, 2002

(86) PCT No.: PCT/GB02/01769

§ 371 (c)(1),
(2), (4) Date: Oct. 16, 2003

(87) PCT Pub. No.: WO02/083729

PCT Pub. Date: Oct. 24, 2002

(65) Prior Publication Data

US 2004/0106552 A1 Jun. 3, 2004

Related U.S. Application Data

(63) Continuation of application No. 09/998,491, filed on Nov. 30, 2001, now Pat. No. 7,491,702.

(30) Foreign Application Priority Data

Apr. 18, 2001 (GB) .................................. 0109558.7
Aug. 17, 2001 (GB) .................................. 0120084.9
Mar. 28, 2002 (GB) .................................. 0207387.2

(51) Int. Cl.
*A61K 38/06* (2006.01)
*A61K 38/07* (2006.01)
*A61K 38/08* (2006.01)
*A61K 47/48* (2006.01)
*C07K 2/00* (2006.01)
*C07K 7/04* (2006.01)
*C07K 5/08* (2006.01)
*C07K 1/00* (2006.01)
*C07K 1/107* (2006.01)

(52) U.S. Cl. .................. 514/18; 514/2; 514/17; 530/300; 530/330; 530/331; 530/333; 530/345

(58) Field of Classification Search .......... None
See application file for complete search history.

(56) References Cited

U.S. PATENT DOCUMENTS

| 660,483 | A | | 10/1900 | Feige et al. ............... 2/114 |
|---|---|---|---|---|
| 4,001,401 | A | * | 1/1977 | Bonsen et al. ............ 514/6 |
| 4,061,736 | A | * | 12/1977 | Morris et al. ............. 514/6 |
| 4,316,891 | A | * | 2/1982 | Guillemin et al. .......... 514/11 |
| 4,565,804 | A | | 1/1986 | Rivier et al. .............. 514/15 |
| 4,707,468 | A | * | 11/1987 | Yoshino et al. ............ 514/16 |
| 4,810,636 | A | * | 3/1989 | Corey ..................... 435/14 |
| 5,028,592 | A | | 7/1991 | Lipton .................... 514/18 |
| 5,493,008 | A | * | 2/1996 | Fox et al. ................. 530/326 |
| 5,597,569 | A | * | 1/1997 | Siegall et al. ............. 424/183.1 |
| 5,639,726 | A | * | 6/1997 | Lawrence et al. .......... 514/12 |
| 5,777,083 | A | * | 7/1998 | Burnie et al. ............. 530/387.3 |
| 5,958,883 | A | | 9/1999 | Snow |
| 6,126,939 | A | | 10/2000 | Eisenbach-Schwartz et al. .......... 424/185.1 |
| 6,214,797 | B1 | * | 4/2001 | Vale et al. ................ 514/12 |
| 2003/0032593 | A1 | * | 2/2003 | Wender et al. ............ 514/12 |
| 2003/0166529 | A1 | * | 9/2003 | Mileusnic et al. .......... 514/12 |

FOREIGN PATENT DOCUMENTS

| JP | 58-183656 | 10/1983 |
|---|---|---|
| WO | WO94/09808 A | 5/1994 |
| WO | WO97/00063 A | 1/1997 |
| WO | WO 97/04748 | 2/1997 |

(Continued)

OTHER PUBLICATIONS

D.A. Kirby, et al. J. Med. Chem. (1995) 38, pp. 4579-4586.*

(Continued)

*Primary Examiner*—Andrew D Kosar
(74) *Attorney, Agent, or Firm*—Daniel A. Monaco; Drinker Biddle & Reath LLP

(57) ABSTRACT

The invention provides a compound having formula $X_1$-Arg-Xaa-Arg-$X_2$ in which $X_1$ and $X_2$ are up to 30 amino acid residues and Xaa is an amino acid residue. A preferred compound is the tripeptide Arg-Glu-Arg which corresponds to amino acid residues 328 to 330 of human amyloid precursor protein. The invention further provides a derivative of a polypeptide having the formula: $X_1$-Arg-Xaa-Arg-$X_2$ wherein $X_1$ and $X_2$, which may be the same or different, each represents from zero to 30 natural or synthetic amino acid residues or derivatives thereof and Xaa represents a natural or synthetic amino acid residue or derivative thereof, at least one functional group of at least one said amino acid residue or derivative thereof being protected by a protective group. The compounds of the invention are believed to be useful in the treatment of Alzheimer's disease and as cognitive enhancers.

17 Claims, 7 Drawing Sheets

FOREIGN PATENT DOCUMENTS

| WO | WO98/09985 A | 3/1998 |
|---|---|---|
| WO | WO98/21327 A | 5/1998 |
| WO | WO99/57305 A | 11/1999 |
| WO | WO 99/58564 | 11/1999 |
| WO | WO 99/67284 | 12/1999 |
| WO | WO 00/06900 | 11/2000 |

OTHER PUBLICATIONS

"Derivative" The On-ine Medical Dictionary. entered Nov. 18, 1997. Accessed Jul. 7, 2005. <http://cancerweb.ncl.ac.uk>> 3 pages.*

Abe, et al.; "Administration of amyloid β-peptides into the medial septum of rats decreases acetylcholine release from hippocampus in vivo"; *Brain Research* 636:162-164 (1994).

Barnes, et al.; "Increased Production of Amyloid Precursor Protein Provides a Substrate for Caspase-3 in Dying Motoneurons"; *The Journal of Neuroscience* 18(15):5869-5880 (Aug. 1, 1998).

Cleary, et al.; "Beta-amyloid (1-40) effects on behavior and memory"; *Brain Research* 682:69-74 (1995).

Coulson, et al.; "What the evolution of the amyloid protein precursor supergene family tells us about its function"; *Neurochemistry International* 36:175-184 (2000).

Curtain, et al.:"Fusogenic activity of amino-terminal region of HIV type 1 Nef protein" *Aids Research And Human Retroviruses* 10(10):1231-40 (Oct. 1994).

Davis, et al.; "Autoradiographic Distribution of L-Proline in Chicks After Intracerebral Injection"; *Physiology & Behavior* 22:693-695 (1979).

Doyle, et al.; "Intraventricular infusions of antibodies to amyloid-β-protein precursor impair the acquisition of a passive avoidance response in the rat"; *Neuroscience Letters* 115 97-102 (1990).

Flood, et al.; "Amnestic effects in mice of four synthetic peptides homologous to amyloid β protein from patients with Alzheimer disease"; *Proc. Natl. Acad. Sci. USA* 88:3363-3366 (Apr. 1991).

Goodman, et al.; "Secreted Forms of β-Amyloid Precursor Protein Protect Hippocampal Neurons against Amyloid β-Peptide-Induced Oxidative Injury"; *Experimental Neurology* 128:1-12 (1994).

Goodman, et al.; "K+ channel openers protect hippocampal neurons against oxidative injury and amyloid β-peptide toxicity"; *Brain Research* 706:328-332 (1996).

Huber, et al.; "Synaptic β-Amyloid Precursor Proteins Increase with Learning Capacity in Rats"; *Neuroscience* 80(2):313-320 (1997).

Huber, et al.; "Involvement of amyloid precursor protein in memory formation in the rat: an indirect antibody approach"; *Brain Research* 603:348-352 (1993).

Ishida, et al.; "Secreted form of β-amyloid precursor protein shifts the frequency dependency for induction of LTD, and enhances LTP in hippocampal slices"; *Neuro Report* 8:2133-2137 (1997).

James, et al.: "Basic amino acids predominate in the sequential autoantigenic determinant of the small nuclear 70K ribonucleoprotein", *Scandinavian Journal Of Immunology* 39(6):557-66 (1994).

Koo, et al., "Amyloid β-protein as a substrate interacts with extracellular matrix to promote neurite outgrowth", *Proc. Natl. Acad. Sci. USA* 90:4748-4752 (May 1993).

Jin, et al.; "Peptides Containing the RERMS Sequence of Amyloid β/A4 Protein Precursor Bind Cell Surface and Promote Neurite Extension"; *The Journal of Neuroscience* 14(9): 5461-5470 (Sep. 1994).

Kang, et al.; "The precursor of Alzheimer's disease amyloid A4 protein resembles a cell-surface receptor"; *Nature* 325(19) (Feb. 1987).

LeBlanc, et al.; "Role of Amyloid Precursor Protein (APP): Study with Antisense Transfection of Human Neuroblastoma Cells"; *Journal of Neuroscience Research* 31:635-645 (1992).

Li, et al.; "Defective Neurite Extension Is Caused by a Mutation in Amyloid β/A4 (Aβ) Protein Precursor Found in Familial Alzheimer's Disease"; *J. Neurobiol.* 32:469-480 (1997).

Lossner, et al.; "Passive Avoidance Training Increases Fucokinase Activity in Right Forebrain Base of Day-Old Chicks"; *Journal of Neurochemistry,* 41:1357-1363 (1983).

Mattson, et al.; "β-Amyloid precursor protein metabolites and loss of neuronal $Ca^{2+}$ homeostasis in Alzheimer's disease"; *TINS* 16(10) (1993).

Mattson, et al.; "Evidence for Excitoprotective and Intraneuronal Calcium-Regulating Roles for Secreted Forms of the β-Amyloid Precursor Protein"; *Neuron* 10:243-254 (Feb. 1993).

Mattson, Mark P.; "Secreted Forms of β-Amyloid Precursor Protein Modulate Dendrite Outgrowth and Calcium Responses to Glutamate in Cultured Embryonic Hippocampal Neurons"; *J. Neurobiol.* 25:439-450 (1994).

Maurice, et al.; "Amnesia induced in mice by centrally administered β-amyloid peptides involves cholinergic dysfunction"; *Brain Research* 706:181-193 (1996).

Merrifield, B: "Solid Phase Synthesis" *Science,* American Association For the Advancement Of Science, US, 232(18)341-347 (Apr. 18, 1986).

Meziane, et al.; "Memory-enhancing effects of secreted forms of the β-amyloid precursor protein in normal and amnestic mice"; *Proc. Natl. Acad. Sci. USA* 95:12683-12688 (Oct. 1998).

Mileusnic, et al.; "APP is required during an early phase of memory formation"; *European Journal of Neuroscience* 12:4487-4495 (2000).

Mucke, et al.; "Synaptotrophic effects of human amyloid β protein precursors in the cortex of transgenic mice"; *Brain Research* 666:151-167 (1994).

Muller, et al.; "Behavioral and Anatomical Deficits in Mice Homozygous for a Modified β-Amyloid Precursor Protein Gene"; *Cell* 79:755-765 (Dec. 2, 1994).

Multhaup, et. al.; "Characterization of the High Affinity Heparin Binding Site of the Alzheimer's Disease βA4 Amyloid Precursor Protein (APP) and its Enhancement by Zinc(II)"; *Journal of Molecular Recognition* 8:247-257 (1995).

Ninomiya, et al.; "Amino Acid Sequence RERMS Represents the Active Domain of Amyloid β/A4 Protein Precursor that Promotes Fibroblast Growth"; *The Journal of Cell Biology,* 121(4): 879-886 (May 1993).

Rist et al: "The bioactive conformation of neuropeptide Y analogues at the human Y-2-receptor", *European Journal Of Biochemistry* 247(3)1019-1028 (1997).

Roch, et al.; "Increase of synaptic density and memory retention by a peptide representing the trophic domain of the amyloid β/A4 protein precursor"; *Proc. Natl. Acad. Sci. USA* 91:7450-7454, (Aug. 1994).

Rose, Steven P.R.; "God's Organism? The Chick as a Model System for Memory Studies"; *Learning and Memory* 7:1-17 (2000).

Sandbrink, et al.; "APP gene family: unique age-associated changes in splicing of Alzheimer's βA4-amyloid protein precursor"; *Neurobiology of Disease* 1:13-24 (1994).

Saitoh, et al.; "Secreted Form of Amyloid β Protein Precursor Is Involved in the Growth Regulation of Fibroblasts"; *Cell* 58:615-622 (Aug. 25, 1989).

Schubert, et al.; "The expression of amyloid beta protein precursor protects nerve cells from β-amyloid and glutamate toxicity and alters their interaction with the extracellular matrix"; *Brain Research* 629:275-282 (1993).

Schubert, et al.; "The Regulation of Amyloid β Protein Precursor Secretion and Its Modulatory Role in Cell Adhesion"; *Neuron* 3:689-694 (Dec. 1989).

Shigematsu, et al.; "Localization of amyloid precursor protein in selective postsynaptic densities of rat cortical neurons"; *Brain Research* 592:353-357(1992).

Storey, et al.; "The amyloid precursor protein of Alzheimer's diesease is found on the surface of static but not actively motile portions of neurites"; *Brain Research* 735:59-66 (1996).

Terranova, et al.; "Administration of amyloid β-peptides in th rat medial septum causes memory deficits: reversal by SR 57746A, a non-peptide neurotrophic compound"; *Neuroscience Letters* 213:79-82 (1996).

Uéda, et al.; "Decreased Adhesiveness of Alzheimer's Disease Fibroblasts: Is Amyloid β-Protein Precursor Involved?"; *Amn. Neurol.,* 25:246-251 (1989).

Yamamoto, et al.; "The Survival of Rat Cerebral Cortial Neurons in the Presence of Trophic APP Peptides"; *J. Neuorbiol.* 25:585-594 (1994).

Zheng, et al.; "β-Amyloid Precursor Protein-Deficient Mice Show Reactive Gliosis and Decreased Locomotor Activity"; *Cell* 81:525-531 (May 19, 1995).

Zheng, et al.; "Mice Deficient for the Amyloid Precursor Protein Gene"; *Ann. NY Acad. Sci.* 777:421-426 (1996).

Kumagai, et al. "Construction of HIV Rev Peptides Containing Peptide Nucleic Acid That Bind HIV RRE IIB RNA", *Bioorganic & Medicinal Chemistry Letters* 10 (2000) 377-379.

Hojo, et al. Protein Synthesis Using S-Alkyl Thioester of Partially Protected Peptide Segments. Synthesis of DNA-Binding Protein of *Bacillus stearothermophilus*, *Bull. Chem. Soc.* Japan, 65, 3055-3063 (1992).

Gururaja, et al. Candidacidal Activity Prompted by N-Terminus Histatin-Like Domain of Human Salivary Mucin (MUC7), *Biochimica et Biophysica Acta* 1431 (1999) 107-119.

Altschul et al., "Basic Local Alignment Search Tool", *J. Mol. Biol.* (1990), 215: 403-410.

Altschul et al., "Gapped BLAST and PSI-BLAST: a new generation of protein database search programs", *Nucl. Acids Res.* (1997), 25(17): 3389-3402.

Beck-Sickinger et al., "Sulfonation of arginine residues as side reaction in Fmoc-peptide synthesis", *Intl. J. Peptide Res.* (1991), 38: 25-31.

Bowness et al., "Identification of T cell receptor recognition residues for a viral peptide presented by HLA B27", *Eur. J. Immunol.* (1994), 24: 2357-2363.

Kirby, et al. "$Y_1$ and $Y_2$ Receptor Selective Neuropeptide Y Analogues: Evidence for a $Y_1$ Receptor Subclass", *J. Med. Chem.* 1995, 38, 4579-4586.

Mileusak et al., "The Role of APP in Memory Formation", Abstract 142.01 Abstract Book p. 314 *Fed. of Eur. Neuroscience Soc.* (FENS), Millenium Meeting, Jun. 24-28, 2000, Brighton, UK.

Mileusnic et al., "The peptide sequence Arg-Glu-Arg, present in the amyloid precursor protein, protects against memory loss caused by Aβ and acts as a cognitive enhancer", *Eur. J. Neuroscience*, (2004) 19: 1933-1938.

Mileusnic et al., "Amyloid Precursor Protein From Synaptic Plasticity to Alzheimer's Disease", *Ann. N.Y. Acad. Sci.* (2005), 1048: 149-165.

Nashabeh et al., "Studies in capillary zone electrophoresis with a post-column multiple capillary device for fraction collection and stepwise increase in electroosmotic flow during analysis", *Electrophoresis*, (1993), 11: 407-416.

*Neural and Behavioral Plasticity, The Use of the Domestic Chick as a Model*, R.J. Andrew, ed., Oxford Univ. Press, Oxford, UK (1991), p. 5-61; 277-305.

Pelsue et al., "Immunoreactivity between a Monolclonal Lupus Autoantibody and the Arginine/Aspartic Acid Repeats Within the U1-snRNP 70K Autoantigen is Conformationally Restricted", *J. of Protein Chem.* (1994), 13(4): 401-408.

Quibell et al., "Solid-phase assembly of backbone amide-protected peptide segments: an efficient and reliable strategy for the synthesis of small proteins", *J. Chem. Soc.*, (1996, Perkin Trans. 1: 1227-1234.

Search Report in European Patent Application 02720228: dated Aug. 11, 2006.

The On-Line Medical Dictionary "Derivative" enterd Nov. 18, 1997 at cancerweb.ncl.ac.uk.

Ukai et al., "Dynorphin A-(1-13) attenuates basal forebrain-lesion-induced amnesia in rats", *Brain Res.*, 625 (1993), p. 355-356.

Wakimasu et al., "Use of the 4-Methoxy-2,6-dimethylbenzenesulfonyl (Mds) Group to Synthesize Dynorphin [1-13] and Related Peptides", *Chem. Pharm. Bull.* (1981), 29(9): 2592-2597.

Wang et al., "Influence of APP17 peptide on the ultrastructure of hippocampus of the D-galactose induced brain aging model mice", *Chinese Pharmacological Bulletin*, Beijing, China (2000) June 16(3), pp. 322-324.

Rong Wang et al., "Effect of App17-mer peptide on glutamate neurotoxicity", *Chinese Pharmacological Bulletin*, Beijing, China (2000) June 16(3), pp. 313-316.

Mark P. Bowes et al., "Reduction of neurological damage by a peptide segment of the amyloid β/A4 protein precursor in a rabbit spinal cord ischemia model", *Experimental Neurology*, University of California, San Diego, La Jolla, CA (1994), pp. 112-119.

\* cited by examiner

```
human  MLPGLALLLLAAWTARALEVPTDGNAGLLAEPQIAMFCGRLNMHMNVQNGKWDSDPSGTKTCIDTK  66 human  EGILQYCQEVYPELQITNVVEANQPVTIQNWCKRGRKQCKTHPHFVIPYRCLVGEFVSDALLVPDK 132 chick  ..............................GMNLHDYGMLLPCGIDKFRGVEFVCCPLAEESDNLDS  37
                                     ||||||||||||||||||||||||||||||||||.||
human  CKFLHQERMDVCETHLHWHTVAKETCSEKSTNLHDYGMLLPCGIDKFRGVEFVCCPLAEESDNVDS 198 chick  ADAEDDDSDVWWGGADADYADGSDDKVVEEQPEEDEELTVVEDEDADDDDDDDGDEI.EETEEEYE 103
       ||||:||||||||||| ||||||:|||| |  ||:|   | |:| ||:||:||||: || || ||
human  ADAEEDDSDVWWGGADTDYADGSEDKVV.EVAEEEEVAEVEEEEADDDEDDEDGDEVEEEAEEPYE 263
                                   ↓
chick  EATERTTSIATTTTTTTESVEEVVRVPTTAASTPDAVDKYLETPGDENEHAHFQKAKERLEAKHRE 168
       |||||||||||||||||||||||||||||||||||||||||||||||||||||||||||||||||
human  EATERTTSIATTTTTTTESVEEVVRVPTTAASTPDAVDKYLETPGDENEHAHFQKAKERLEAKHRE.329 chick  RMSQVMREWEEAERQAKNLPKADKKAVIQHFQEKVESLEQEAANERQQLVETHMARVEAMLNDRRR 234
       |||||||||||||||||||||||||||||||||||||||||||||||||||||||||||||||||
human  RMSQVMREWEEAERQAKNLPKADKKAVIQHFQEKVESLEQEAANERQQLVETHMARVEAMLNDRRR 395 chick  IALENYITALQTVPPRPRHVFNMLKKYVRAEQKDRQHTLKHFEHVRMVDPKKAAQIRSQVMTHLRV 300
       :|||||||||| |||||||||||||||||||||||||||||||||||||||||||||||||||||
human  LALENYITALQAVPPRPRHVFNMLKKYVRAEQKDRQHTLKHFEHVRMVDPKKAAQIRSQVMTHLRV 461 chick  IYERMNQSLSFLYNVPAVAEEIQDEVDELLQKEQNYSDDVLANMISEPRISYGNDALMPSLTETKT 365
       |||||||||| ||||||||||||||||||||||||||||||||||||||||||||||||||||||
human  IYERMNQSLSLLYNVPAVAEEIQDEVDELLQKEQNYSDDVLANMISEPRISYGNDALMPSLTETKT 527 chick  TVELLPVDGEFSLDDLQPWHPFGVDSVPANTENEVEPVDARPAADRGLTTRPGSGLTNVKTEEVSE 432
       |||||||.||||||||||| || ||||||||||||||||||||||||||||||||||:||||:||
human  TVELLPVNGEFSLDDLQPWHSFGADSVPANTENEVEPVDARPAADRGLTTRPGSGLTNIKTEEISE 593 chick  VKMDAEFRHDSGYEVHHQKLVFFAEDVGSNKGAIIGLMVGGVVIATVIVITLVMLKKKQYTSIHHG 498
       |||||||||||||||||||||||||||||||||||||||||||||||||||||||||||||||||
human  VKMDAEFRHDSGYEVHHQKLVFFAEDVGSNKGAIIGLMVGGVVIATVIVITLVMLKKKQYTSIHHG 659 chick  VVEVDAAVTPEERHLSKMQQNGYENPTYKFFEQMQN*  534
       |||||||||||||||||||||||||||||||||||||
human  VVEVDAAVTPEERHLSKMQQNGYENPTYKFFEQMQN*  695
```

FIG. 1

POLYPEPTIDES, DERIVATIVES AND USES THEREOF

FIELD OF THE INVENTION

The present invention relates to polypeptide compounds, to compounds derived therefrom and to the use of such compounds in medicine. Compounds according to the invention are believed to be potentially useful as cognitive enhancers and in the treatment of neurodegenerative diseases such as Alzheimer's disease.

BACKGROUND TO THE INVENTION

Alzheimer's disease is a degenerative brain disease which is characterised by progressive loss of memory and subsequently most other cognitive functions in an irreversible decline over a period of years. It represents a substantial health problem, particularly in an ageing population.

The amyloid precursor protein ("APP") is a multifunctional transmembrane protein and is known to have important functions in normal brain tissue. The human form of APP is known to consist of 695 amino acid residues (SEQ ID No: 1) in a sequence which is also known (see Kang et al, Nature 325, 733-736 (1987), the contents of which are incorporated herein by reference). The chick form of APP is known to consist of 534 amino acid residues (SEQ ID No: 2) and to resemble the human form closely, being approximately 95% homologous therewith (see the paper by Kang et al just mentioned and Barnes et al, J Neurosci, 18 (15) 5869-5880 (1998), contents of which are also incorporated herein by reference). The amino acid sequences of the human and chick forms of APP are reproduced in FIG. 1 of the drawings of this specification.

Two effects which have been noted to take place in the brain of a person suffering from Alzheimer's disease are the build up outside the nerve cells of the brain of tangled masses of protein and the build up inside the brain cells of a different protein. The extracellular proteins are known to be aggregates of polypeptides having amino acid sequences corresponding to portions of the extracellular part of APP. The tangled masses of these proteins are known as amyloid plaques. The intracellular proteins are known as tau proteins. It is however not known whether either or both of the extracellular accumulation of amyloid plaques and the intracellular accumulation of tau proteins are the causes or the symptoms of Alzheimer's and related neurodegenerative diseases of the Alzheimer type.

The amino acid sequence of the β-amyloid polypeptide fragment (1-42) is identical in the human and chick forms of APP and consists of amino acid residues 597 to 638 in the human form and residues 436 to 477 in the chick form, (see the papers by Kang et al and Barnes et al referred to hereinbefore).

DEFINITIONS

The following expressions are used in this specification and have the following meanings, except where the context indicates otherwise:

| | |
|---|---|
| APP | means "amyloid precursor protein"; |
| human APP | means the human form of APP; |
| chick APP | means the chick form of APP; |
| RERMS | means the pentapeptide Arg-Glu-Arg-Met-Ser (SEQ ID No.:3); |
| APP 328-332 | also means the pentapeptide Arg-Glu-Arg-Met-Ser (SEQ ID No.:3) which corresponds to amino acid residues 328 to 332 of human APP; |
| SMRER | means the pentapeptide Ser-Met-Arg-Glu-Arg (SEQ ID No.:4); |
| APP 332-328 | means the same as SMRER; (SEQ ID NO.:4) |
| Aβ domain | means the domain of APP which forms β-amyloid plaques; |
| β-amyloid 12-28 | means the sequence of amino acid residues which constitute part of the Aβ domain of human APP, the sequence being Val-His-His-Gln-Lys-Leu-Val-Phe-Phe-Ala-Glu-Asp-Val-Gly-Ser-Asn-Lys (SEQ ID No: 8) which corresponds to amino acid residues 608 to 624 of human APP and amino acids 447 to 463 of chick APP; |
| RSAER | means the pentapeptide Arg-Ser-Ala-Glu-Arg (SEQ ID NO.:5); |
| APP 319-335 | means the polypeptide Ala-Lys-Glu-Arg-Leu-Glu-Ala-Lys-His-Arg-Glu-Arg-Met-Ser-Gln-Val-Met (AKERLEAKHRERMSQVM) (SEQ ID No:6); |
| RER | means the tripeptide Arg-Glu-Arg (SEQ ID No:9); |
| APP 328-330 | means the same as RER (SEQ ID NO.:9); |
| Ac-RER | means RER (SEQ ID NO.:9) in which one of the hydrogen atoms of the —NH₂ group at the N-terminus has been replaced by an acetyl group; the structural formula of Ac-RER is given hereinbelow; |
| RERM | means the tetrapeptide Arg-Glu-Arg-Met (SEQ ID No: 10); |
| APP 328-331 | means the same as RERM (SEQ ID NO.:10); |
| MRER | means the tetrapeptide Met-Arg-Glu-Arg (SEQ ID No: 11); |
| APP 331-328 | means the same as MRER (SEQ ID NO.:11); |
| amino acid | as used herein is meant to include both natural and synthetic amino acids, and both D and L amino acids; |
| standard amino acid | means any of the twenty standard L-amino acids commonly found in naturally occurring peptides; |
| nonstandard amino acid | means any amino acid, other than the standard amino acids, regardless of whether it is prepared synthetically or derived from a natural source; as used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity; additionally, a disulfide linkage may be present or absent in the peptides of the invention; |
| derivative | includes any purposefully generated peptide which in its entirety, or in part, has a |

-continued

| | substantially similar amino acid sequence to the present compounds; derivatives of the present compounds may be characterized by single or multiple amino acid substitutions, deletions, additions, or replacements; these derivatives may include (a) derivatives in which one or more amino acid residues of the present compounds are substituted with conservative or non-conservative amino acids; (b) derivatives in which one or more amino acids are added to the present compounds; (c) derivatives in which one or more of the amino acids of the present compounds include a substituent group; (d) derivatives in which the present compounds or a portion thereof is fused to another peptide (e.g., serum albumin or protein transduction domain); (e) derivatives in which one or more nonstandard amino acid residues (i.e., those other than the 20 standard L-amino acids found in naturally occurring proteins) are incorporated or substituted into the present compounds sequence; and (f) derivatives in which one or more nonamino acid linking groups are incorporated into or replace a portion of the present compounds; |
|---|---|
| APP 296-335, APP 317-332, APP 321-335, APP 319-332, APP 321-332, APP 321-331, APP 325-335, APP 321-330, APP 327-332 and APP 316-337 | have the meanings given in tables 1 and 2 hereinafter. |

Throughout this specification and its claims amino acid sequences are written using the standard one-letter or three-letter abbreviations. All sequences are written from left to right in the direction from the N-terminus to the C-terminus.

The following term is defined as follows:

| reverse order sequence | as used herein, the reverse order sequence of a given sequence is a sequence in which the order of amino acid residues is reversed compared with the given sequence when reading in the direction from the N-terminus to the C-terminus and vice versa; thus, for example, SMRER (SEQ ID NO.:4) is the reverse order sequence of RERMS (SEQ ID NO.:3), each being read as stated above from left to right in the N-terminal to C-terminal direction; further, MVQSMRERHKAELREKA (SEQ ID No: 7) (also referred to herein as APP 335-319) is the reverse order sequence of APP 319-335 defined above. |
|---|---|

WO-A-94/09808 (The Regents of The University of California, inventor T Saito) and T Saito and various co-authors in J. Neuroscience 14 5461-5470 (1994), J. Neuobiol. 25, 585-594 (1994) and J. Cell Biol. 121, 879-886 (1993) disclose certain polypeptides corresponding to parts of human APP. These polypeptides consist of the following:

TABLE 1

| no. of amino acid residues | corresponding part of human APP | sequence | SEQ ID NO. |
|---|---|---|---|
| 40 | APP 296-335 | TPDAVDKYLETPGDENEHAHF QKAKERLEAKHRERMSQVM [Thr-Pro-Asp-Ala-Val-Asp-Lys-Tyr-Leu-Glu-Thr-Pro-Gly-Asp-Glu-Asn-Glu-His-Ala-His-Phe-Gln-Lys-Ala-Lys-Glu-Arg-Leu-Glu-Ala-Lys-His-Arg-Glu-Arg-Met-Ser-Gln-Val-Met] | 22 |
| 17 | APP 319-335 | AKERLEAKHRERMSQVM [Ala-Lys-Glu-Arg-Leu-Glu-Ala-Lys-His-Arg-Glu-Arg-Met-Ser-Gln-Val-Met] | 6 |
| 16 | APP 317-332 | QKAKERLEAKHRERMS [Gln-Lys-Ala-Lys-Glu-Arg-Leu-Glu-Ala-Lys-His-Arg-Glu-Arg-Met-Ser] | 12 |
| 15 | APP 321-335 | ERLEAKHRERMSQVM [Glu-Arg-Leu-Glu-Ala-Lys-His-Arg-Glu-Arg-Met-Ser-Gln-Val-Met] | 13 |
| 14 | APP 319-332 | AKERLEAKHRERMS [Ala-Lys-Glu-Arg-Leu-Glu-Ala-Lys-His-Arg-Glu-Arg-Met-Ser] | 14 |
| 12 | APP 321-332 | ERLEAKHRERMS [Glu-Arg-Leu-Glu-Ala-Lys-His-Arg-Glu-Arg-Met-Ser] | 15 |
| 11 | APP 321-331 | ERLEAKHRERM [Glu-Arg-Leu-Glu-Ala-Lys-His-Arg-Glu-Arg-Met] | 16 |
| 11 | APP 325-335 | AKHRERMSQVM [Ala-Lys-His-Arg-Glu-Arg-Met-Ser-Gln-Val-Met] | 17 |
| 10 | APP 321-330 | ERLEAKHRER [Glu-Arg-Leu-Glu-Ala-Lys-His-Arg-Glu-Arg] | 18 |
| 6 | APP 327-332 | HRERMS [His-Arg-Glu-Arg-Met-Ser] | 19 |
| 5 | APP 328-332 | RERMS [Arg-Glu-Arg-Met-Ser] | 3 |
| 4 | APP 328-331 | RERM [Arg-Glu-Arg-Met] | 10 |
| 3 | APP 328-330 | RER [Arg-Glu-Arg] | 9 |

The same publications also refer to a 17-mer polypeptide which is the reverse-order sequence of APP 319-335 (as defined above). The reverse order sequence is also identified herein as APP 335-319.

G Multhorp et al is J. Mol Recognition 8, 247-257 (1995) disclose the following polypeptide which also corresponds to part of human APP:

TABLE 2

| No. of amino acid residues | corresponding part of human APP | Sequence | SEQ ID NO. |
|---|---|---|---|
| 22 | APP 316-337 | FQKAKERLEAKHRERM SQVMRE [Phe-Gln-Lys-Ala-Lys- Glu-Arg-Leu-Glu-Ala- Lys-His-Arg-Glu-Arg- Met-Ser-Gln-Val-Met- Arg-Glu] | 20 |

SUMMARY OF THE INVENTION

The present invention provides a derivative of a polypeptide having the formula:

$$X_1\text{-Arg-Xaa-Arg-}X_2 \quad (I)$$

wherein $X_1$ and $X_2$, which may be the same or different, each represents from zero to 30 natural or synthetic amino acid residues or derivatives thereof and Xaa represents a natural or synthetic amino acid residue or a derivative thereof, at least one functional group of at least one said amino acid residue or derivative thereof being protected by a protective group.

Preferably, the protected functional group(s) comprise one or more amino groups.

Advantageously, the amino group(s) comprise an N-terminal amino group.

Conveniently, at least one protected amino group is protected by replacement of only one of its hydrogen atoms by a protective group.

In other polypeptide derivatives, the protected functional group(s) comprise one or more carboxyl groups.

Advantageously, the carboxyl group(s) comprise a C-terminal carboxyl group.

Advantageously, the or each protective group is an acyl group represented by the formula

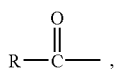

wherein R represents a straight- or branched-chain alkyl group, for example a methyl, ethyl, n-propyl, isopropyl, n-butyl, isobutyl, s-butyl, t-butyl, pentyl or hexyl group, a substituted or unsubstituted cycloalkyl group, for example a methylcyclohexyl or cyclohexyl group, a substituted or unsubstituted straight- or branched-chain aralkyl group, for example a benzyl group, or a substituted or unsubstituted aryl group, for example a phenyl or tolyl group. Examples of substituents in the substituted groups mentioned above are the alkyl groups also mentioned above.

Straight- or branched-chain alkyl groups are most preferred for R, methyl groups being particularly preferred.

In formula (I), amino acid derivatives include, for example, substituted amino acids.

In formula (I), $X_1$ and $X_2$ are each preferably independently from zero to 20, more preferably from zero to 10.

When $X_1$ and $X_2$ are both zero in formula (I), formula (I) is that of a tripeptide derivative which is preferably Ac-RER when Xaa is glutamic acid.

Preferably, compounds according to the invention are compounds in which $X_1$ and $X_2$ are such that formula (I) represents an amino acid sequence which is identical or closely homologous to amino acid residues 328 to 332 of human APP and up to 30 successive amino acid residues of human APP extending in each direction therefrom, or to a sequence which is closely homologous thereto or in which the amino acids thereof are replaced by nonstandard amino acids.

It is also preferred that formula (I) is one in which $X_1$ and $X_2$ are such that the formula represents a reverse-order amino acid sequence which is identical or closely homologous to amino acid residues 330 to 328 of human APP and up to 30 successive amino acid residues of human APP extending in each direction therefrom, or to a sequence which is closely homologous thereto or in which the amino acids thereof are replaced by nonstandard amino acids.

As used herein, a peptide or a portion of a peptide which is "closely homologous" means the peptide, or the portion thereof, has an amino acid homology of greater than about 80% with respect to a reference peptide, preferably greater than about 90% and, more preferably, greater than about 95%.

Amino acid sequence homology may be computed by using the BLASTP and TBLASTN programs which employ the BLAST (basic local alignment search tool) 2.0.14 algorithm; BLASTP and TBLASTN settings to be used in such computations are indicated in table 3 below. Amino acid sequence identity (complete homology) is reported under "Identities" by the BLASTP and TBLASTN programs. Amino acid sequence similarity (degree of homology) is reported under "Positives" by the BLASTP and TBLASTN programs. Techniques for computing amino acid sequence homology are well known to those skilled in the art, and the use of the BLAST algorithm is described in Altschul et al. (1990), *J. Mol. Biol.* 215: 403-10 and Altschul et al. (1997), *Nucleic Acids Res.* 25:3389-3402, the disclosures of which are herein incorporated by reference in their entirety. BLASTP and TBLASTN programs utilizing the BLAST 2.0.14 algorithm and may be accessed on the World Wide Web at the National Center for Biotechnology Information website under the National Institutes for Health domain.

TABLE 3

Settings to be used for the computation of amino acid sequence similarity or identity with BLASTP and TBLASTN programs utilizing the BLAST 2.0.14 algorithm

| | |
|---|---|
| Expect Value | 10 |
| Filter | Low complexity filtering using SEG program* |
| Substitution Matrix | BLOSUM62 |
| Gap existence cost | 11 |
| Per residue gap cost | 1 |
| Lambda ratio | 0.85 |
| Word size | 3 |

*The SEG program is described by Wootton and Federhen (1993), Comput. Chem. 17: 149-163.

Preferably, $X_1$ in formula (I) represents:

$X_3$-Ala-Lys-Glu-Arg-Leu-Glu-Ala-Lys-His     (SEQ ID NO.:23)

wherein $X_3$ represents from zero to 21 natural or synthetic amino acid residues or derivatives thereof, and/or $X_2$ represents Met-Ser-Gln-Val-Met-$X_4$     (SEQ ID NO.:24)

wherein $X_4$ represents from zero to 25, natural or synthetic amino acid residues or derivatives thereof.

$X_3$ and $X_4$ are again preferably each independently from zero to 20, more preferably from zero to 10.

When $X_3$ and $X_4$ are both zero and Xaa is glutamic acid, the amino acid residues of the formula corresponds to the sequence of amino acid residues 319 to 335 of human APP.

It is also preferred that $X_1$ in (I) represents:

$X_3$-Met-Val-Gln-Ser-Met (SEQ ID NO.:25)

wherein $X_3$ represents from zero to 25, natural or synthetic amino acid residues or derivatives thereof, and/or $X_2$ represents:

His-Lys-Ala-Glu-Leu-Arg-Glu-Lys-Ala-$X_4$ (SEQ ID NO.:26)

wherein $X_4$ represents from zero to 21, natural or synthetic amino acid residues or derivatives thereof.

$X_3$ and $X_4$ are again preferably independently each from zero to 20, more preferably from zero to 10.

When $X_3$ and $X_4$ are both zero and Xaa is glutamic acid, the amino acid residues of the formula corresponds to the reverse-order sequence of amino acid residues 335 to 319 of human APP.

The invention also provides compounds of formula (I) in which $X_2$ represents:

Met-$X_4$ wherein $X_4$ represents from zero to 29 natural or synthetic amino acid residues or derivatives thereof.

In such compounds, $X_2$ preferably represents:

Met-Ser-$X_4$ wherein $X_4$ represents from zero to 28 natural or synthetic amino acid residues or derivatives thereof.

Further, the invention provides compounds of formula (I) in which $X_1$ represents:

$X_3$-Met wherein $X_3$ represents from zero to 29 natural or synthetic amino acid residues or derivatives thereof.

In such compounds, $X_1$ preferably represents:

$X_3$-Ser-Met wherein $X_3$ represents from zero to 28 natural or synthetic amino acid residues or derivatives thereof.

The invention thus provides derivatives of the stated kind of the peptides RER (SEQ ID NO.:9), RERM (SEQ ID NO.:10), MRER (SEQ ID NO.:11), RERMS (SEQ ID NO.:3) and SMRER (SEQ ID NO.:4).

The most preferred of such derivatives is the compound Ac-RER which has the structural formula:

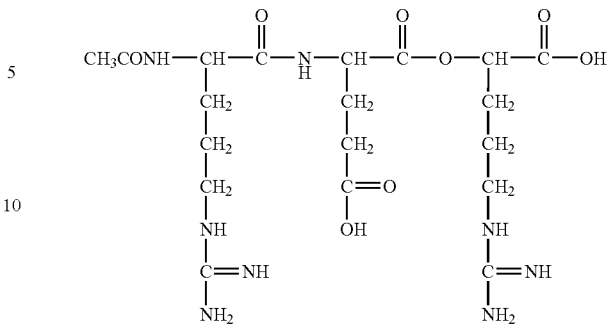

In addition to the compounds mentioned hereinbefore, the present invention also provides the compounds (including the stated derivatives of RER (SEQ ID NO.:9), RERM (SEQ ID NO.:10), MRER (SEQ ID NO.:11), SMRER (SEQ ID NO.:4) and RERMS (SEQ ID NO.:3)) for use in medicine and their use in the preparation of medicaments for the treatment of neurodegenerative diseases, including Alzheimer's disease, and as cognitive enhancers.

The invention further provides pharmaceutical compositions comprising the compounds (including the stated derivatives of RER (SEQ ID NO.:9), RERM (SEQ ID NO.:10), MRER (SEQ ID NO.:11), SMRER (SEQ ID NO.:4) and RERMS (SEQ ID NO.:3)) and a pharmaceutically-acceptable carrier and also compositions in which a compound according to the invention (including the stated derivatives of RER (SEQ ID NO.:9), RERM (SEQ ID NO.:10), MRER (SEQ ID NO.:11), SMRER (SEQ ID NO.:4) and RERMS (SEQ ID NO.:3)) is chemically or physically linked to a further molecule or vehicle to form a complex for pharmaceutical delivery of the compound.

Further, the invention provides a method of treatment of a neurodegenerative disease in a human or non-human animal suffering or potentially suffering from the disease is administered with an amount of a composition referred to in the preceding paragraph or a compound according to the present invention effective to treat the disease. The invention also provides a method of producing a cognitive enhancement in a human or non-human animal by administering to the animal a said composition or compound in an amount effective to produce the enhancement.

The compounds which are most preferred in the medical uses and pharmaceutical compositions are the stated derivatives of the following:

Arg-Glu-Arg (SEQ ID No: 9)

which corresponds to amino acid residues 328-330 of human APP,

Arg-Glu-Arg-Met (SEQ ID No: 10)

which corresponds to amino acid residues 328-331 of human APP,

Met-Arg-Glu-Arg (SEQ ID No: 11)

which is the reverse-order polypeptide corresponding to the above,

Arg-Glu-Arg-Met-Ser (SEQ ID No: 3)

which corresponds to amino acid residues 328-332 of human APP,

Ser-Met-Arg-Glu-Arg (SEQ ID No: 4)

which is the reverse-order polypeptide corresponding to the above,

Ala-Lys-Glu-Arg-Leu-Glu-Ala-Lys-His- (SEQ ID No: 6)
Arg-Glu-Arg-Met-Ser-Gln-Val-Met which corresponds to amino acid residues 319-335 of human APP, and Met-Val-Gln-Ser-Met-Arg-Glu-Arg-His- (SEQ ID No: 7)
Lys-Ala-Glu-Leu-Arg-Glu-Lys-Ala which is the reverse-order polypeptide corresponding to the above.

The present invention also provides a compound having a formula comprising:

$X_1$-Arg-Glu-Arg-$X_2$ (II)

wherein $X_1$ and $X_2$, which may be the same or different, each represents from zero to 32 natural or synthetic amino acid residues or derivatives thereof, and Xaa represents a natural or synthetic amino acid residue or a derivative thereof, it being preferred that the compound is none of the following (as hereinbefore defined): APP 296-335, APP 319-335, APP 317-332, APP 321-335, APP 319-332, APP 321-332, APP 321-331, APP 325-335, APP 321-330, APP 327-332, APP 328-332, APP 328-331, APP 328-330, APP 335-319 and APP 316-337.

In formula (II), $X_1$ and $X_2$ are preferably and independently each from zero to 22, more preferably from zero to 12. Most preferably, one or both of $X_1$ and $X_2$ is zero.

Preferably, $X_1$ and $X_2$ are such that formula (II) represents an amino acid sequence which is identical or closely homologous to amino acid residues 328 to 330 of human APP and up to 32 successive amino acid residues of human APP extending in each direction therefrom, the formula also comprising sequences closely homologous to said sequence and sequences in which said amino acids thereof are replaced by nonstandard amino acids and/or by derivatives of acid amino acids.

It is also preferred that $X_1$ and $X_2$ are such that formula (II) represents a reverse-order amino acid sequence which is identical or closely homologous to amino acid residues 330 to 328 of human APP and up to 32 successive amino acid residues of human APP extending in each direction therefrom, the formula also comprising sequences closely homologous to said reverse-order sequence and sequences in which said amino acids thereof are replaced by nonstandard amino acids and/or by derivatives of acid amino acids.

The invention further provides a compound having a formula comprising:

$X_1$-Arg-Xaa-Arg-$X_2$ (III)

wherein $X_1$ and $X_2$, which may be the same or different, each represents from zero to 32 natural or synthetic amino acid residues or derivatives thereof and Xaa represents a natural or synthetic amino acid residue or a derivative thereof, for use in medicine.

In formula (III), $X_1$ and $X_2$ are preferably independently each from zero to 22, more preferably from zero to 12. Most preferably, one or both of $X_1$ and $X_2$ is zero.

Preferably, $X_1$ and $X_2$ are such that formula (III) represents an amino acid sequence which is identical or closely homologous to amino acid residues 328 to 330 of human APP and up to 32 successive amino acid residues of human APP extending in each direction therefrom, the formula also comprising sequences closely homologous to said sequence and sequences in which said amino acids thereof are replaced by nonstandard amino acids and/or by derivatives of acid amino acids.

It is also preferred that $X_1$ and $X_2$ are such that formula (III) represents a reverse-order amino acid sequence which is identical or closely homologous to amino acid residues 330 to 328 of human APP and up to 30 successive amino acid residues of human APP extending in each direction therefrom, the formula also comprising sequences closely homologous to said reverse-order sequence and sequences in which said amino acids thereof are replaced by nonstandard amino acids and/or by derivatives of acid amino acids.

A particularly preferred compound is one in which $X_1$ and $X_2$ represents:

$X_3$-Ala-Lys-Glu-Arg-Leu-Glu-Ala-Lys-His (SEQ ID NO.:27)

wherein $X_3$ represents from zero to 23 natural or synthetic amino acid residues or derivatives thereof, and/or $X_2$ represents:

Met-Ser-Gln-Val-Met-$X_4$ (SEQ ID NO.:28)

wherein $X_4$ represents from zero to 27 natural or synthetic amino acid residues or derivatives thereof.

Another preferred compound is one in which $X_1$ and $X_2$ represents:

$X_3$-Met-Val-Gln-Ser-Met (SEQ ID NO.:29)

wherein $X_3$ represents from zero to 27 natural or synthetic amino acid residues or derivatives thereof, and/or $X_2$ represents:

His-Lys-Ala-Glu-Leu-Arg-Glu-Lys-Ala-$X_4$ (SEQ ID NO.:30)

wherein $X_4$ represents from zero to 23 natural or synthetic amino acid residues or derivatives thereof.

In such compounds, $X_3$ and $X_4$ are preferably independently each from zero to 20, more preferably from zero to 10. Most preferably, one or both of $X_3$ and $X_4$ is zero.

Xaa in formulae (I) and (III) is preferably glutamic acid.

The present invention also provides the use of a compound having a formula comprising:

$X_1$-Arg-Xaa-Arg-$X_2$ (III)

wherein $X_1$ and $X_2$, which may be the same or different, each represents from zero to 32 natural or synthetic amino acid residues or derivatives thereof and Xaa represents a natural or synthetic amino acid residue or a derivative thereof, in the preparation of a medicament for use in the treatment of a neurodegenerative disease or as a cognitive enhancer.

In addition, the invention provides a pharmaceutical composition comprising such a compound and a pharmaceutically acceptable carrier.

Moreover, the invention provides a said compound which is chemically or physically linked to a further molecule or vehicle to form a complex for pharmaceutical delivery of the compound.

Furthermore, the invention provides methods of treating a neurodegenerative disease or of obtaining a cognitive enhancement in a human or non-human animal by administering to the animal an effective amount of a compound according to the invention, optionally in the form of a pharmaceutical composition as referred to.

The present invention provides a compound having a formula comprising:

$$X_1\text{-Arg-Xaa}_1\text{-Arg-Xaa}_2\text{-Xaa}_3\text{-}X_2 \qquad (IV)$$

wherein $X_1$ and $X_2$, which may be the same or different, each represents from zero to 30 natural or synthetic amino acid residues or derivatives thereof and $Xaa_1$, $Xaa_2$ and $Xaa_3$, which may be the same or different, each represents a natural or synthetic amino acid or a derivative thereof.

The amino acid derivatives include, for example, substituted amino acids.

$X_1$ and $X_2$ are each preferably from zero to 20, more preferably from zero to 10.

When $X_1$ and $X_2$ are both zero, the formula is that of a pentapeptide which is RERMS (SEQ ID NO.:3) when $Xaa_1$ is glutamic acid, $Xaa_2$ is methionine and $Xaa_3$ is serine.

In a compound according to the invention, $Xaa_1$ is preferably glutamic acid, $Xaa_2$ is preferably methionine and $Xaa_3$ is preferably serine.

Preferably, the compound is one in which $X_1$ and $X_2$ are such that (IV) represents an amino acid sequence which is identical or closely homologous to amino acid residues 328 to 332 of human APP and up to 30 successive amino acid residues of human APP extending in each direction therefrom.

The degree of homology is preferably at least 80%, more preferably at least 90% and, most preferably, at least 95%.

The invention also provides compounds having a formula comprising:

$$X_1\text{-Xaa}_3\text{-Xaa}_2\text{-Arg-Xaa}_1\text{-Arg-}X_2 \qquad (V)$$

wherein $X_1$, $X_2$, $Xaa_1$, $Xaa_2$ and $Xaa_3$ are as stated hereinbefore.

When $X_1$ and $X_2$ are both zero, the formula is that of a pentapeptide which is SMRER (SEQ ID NO.:4) when $Xaa_1$ is glutamic acid, $Xaa_2$ is methionine and $Xaa_3$ is serine.

Such formulae represent the reverse-order sequences of the formulae mentioned hereinbefore.

Preferably, the compound is one in which $X_1$ and $X_2$ are such that the formula represents a reverse-order amino acid sequence which is identical or closely homologous to amino acid residues 332 to 328 of human APP and up to 30 successive amino acid residues of human APP extending in each direction therefrom.

The degree of homology is again preferably at least 80%, more preferably at least 90% and, most preferably, at least 95%.

Preferably, $X_1$ in (IV) represents:

$X_3$-Ala-Lys-Glu-Arg-Leu-Glu-Ala-Lys-His (SEQ ID NO.:31)

and/or $X_2$ represents

Gln-Val-Met-$X_4$ $X_3$ and $X_4$ being the same or different and representing from zero to 30 natural or synthetic amino acid residues or derivatives thereof.

$X_3$ and $X_4$ are again preferably each from zero to 20, more preferably from zero to 10.

When $X_3$ and $X_4$ are both zero and $Xaa_1$, $Xaa_2$ and $Xaa_3$ are glutamic acid, methionine and serine, respectively, the formula corresponds to the sequence of amino acid residues 319 to 335 of human APP.

Preferably, $X_1$ in (V) represents:

$X_3$-Met-Val-Gln and/or $X_2$ represents:

His-Lys-Ala-Glu-Leu-Arg-Glu-Lys-Ala-$X_4$ (SEQ ID NO.:32)

wherein $X_3$ and $X_4$, which may be the same or different, each represents from zero to 30 natural or synthetic amino acid residues or derivatives thereof.

$X_3$ and $X_4$ are again preferably each from zero to 20, more preferably from zero to 10.

When $X_3$ and $X_4$ are both zero and $Xaa_1$, $Xaa_2$ and $Xaa_3$ are glutamic acid, methionine and serine, respectively, the formula corresponds to the reverse-order sequence of amino acid residues 335 to 319 of human APP.

In addition to the compounds mentioned hereinbefore, the present invention also provides the compounds (including RERMS (SEQ ID NO.:3) and SMRER (SEQ ID NO.:4)) for use in medicine and their use in the preparation of medicaments for the treatment of neurodegenerative diseases, including Alzheimer's disease, and as cognitive enhancers.

The invention further provides pharmaceutical compositions comprising the compounds (including RERMS (SEQ ID NO.:3) and SMRER (SEQ ID NO.:4)) and a pharmaceutically-acceptable carrier and also compositions in which a compound according to the invention (including RERMS (SEQ ID NO.:3) and SMRER (SEQ ID NO.:4)) is chemically or physically linked to a further molecule or vehicle to form a complex for pharmaceutical delivery of the compound.

The compounds which are most preferred in the medical uses and pharmaceutical compositions are the following:

Arg-Glu-Arg-Met-Ser (SEQ ID No:3)

which corresponds to amino acid residues 328-332 of human APP,

Ser-Met-Arg-Glu-Arg (SEQ ID No:4)

which is the reverse-order polypeptide of the above,

```
Ala-Lys-Glu-Arg-Leu-Glu-Ala-Lys-His-   (SEQ ID No: 6)
Arg-Glu-Arg-Met-Ser-Gln-Val-Met
``` which corresponds to amino acid residues 319-335 of human APP, and

```
Met-Val-Gln-Ser-Met-Arg-Glu-Arg-His-   (SEQ ID No: 7)
Lys-Ala-Glu-Leu-Arg-Glu-Lys-Ala
``` which is the reverse-order polypeptide of the above.

The present invention provides a compound having a formula comprising:

$$X_1\text{-Arg-Xaa-Arg-}X_2 \qquad (VI)$$

wherein $X_1$ and $X_2$, which may be the same or different, each represents from zero to 30 natural or synthetic amino acid residues or derivatives thereof and Xaa represents a natural or synthetic amino acid or a derivative thereof. Xaa is preferably glutamic acid.

The amino acid derivatives include, for example, substituted amino acids.

$X_1$ and $X_2$ are each preferably from zero to 20, more preferably from zero to 10.

When $X_1$ and $X_2$ are both zero, the formula is that of a tripeptide which is Arg-Glu-Arg (RER (SEQ ID NO.:9)) when Xaa is glutamic acid.

Preferably, the compound is one in which $X_1$ and $X_2$ are such that (I) represents an amino acid sequence which is identical or closely homologous to amino acid residues 328 to 330 of human APP and up to 30 successive amino acid residues of human APP extending in each direction therefrom.

It is also preferred that the compound is one in which $X_1$ and $X_2$ are such that the formula represents a reverse-order amino acid sequence which is identical or closely homologous to amino acid residues 330 to 328 of human APP and up to 30 successive amino acid residues of human APP extending in each direction therefrom.

In each case, the degree of homology is again preferably at least 80%, more preferably at least 90% and, most preferably, at least 95%.

Preferably, $X_1$ in (VI) represents:

$X_3$-Ala-Lys-Glu-Arg-Leu-Glu-Ala-Lys-His (SEQ ID NO.:31)

and/or $X_2$ represents

Met-Ser-Gln-Val-Met-$X_4$ (SEQ ID NO.:33)

$X_3$ and $X_4$ being the same or different and representing from zero to 30 natural or synthetic amino acid residues or derivatives thereof.

$X_3$ and $X_4$ are again preferably each from zero to 20, more preferably from zero to 10.

When $X_3$ and $X_4$ are both zero and Xaa is glutamic acid, the formula corresponds to the sequence of amino acid residues 319 to 335 of human APP.

It is also preferred that $X_1$ in (VI) represents:

$X_3$-Met-Val-Gln-Ser-Met (SEQ ID NO.:34)

and/or $X_2$ represents:

His-Lys-Ala-Glu-Leu-Arg-Glu-Lys-Ala-$X_4$ (SEQ ID NO.:32)

wherein $X_3$ and $X_4$, which may be the same or different, each represents from zero to 30 natural or synthetic amino acid residues or derivatives thereof.

$X_3$ and $X_4$ are again preferably each from zero to 20, more preferably from zero to 10.

When $X_3$ and $X_4$ are both zero and Xaa is glutamic acid, the formula corresponds to the reverse-order sequence of amino acid residues 335 to 319 of human APP.

The invention also provides compounds having the formula (VI) in which Xaa is glutamic acid and either $X_1$ is methionine and $X_2$ is zero, or $X_1$ is zero and $X_2$ is methionine. These are the compounds Met-Arg-Glu-Arg (MRER) (SEQ ID No: 11) and Arg-Glu-Arg-Met (RERM) (SEQ ID No: 10), respectively.

The present invention also provides the compounds mentioned above (including RER (SEQ ID NO.:9)) for use in medicine and their use in the preparation of medicaments for the treatment of neurodegenerative diseases, including Alzheimer's disease, and as cognitive enhancers.

The invention further provides pharmaceutical compositions comprising the compounds (including RER (SEQ ID NO.:9)) and a pharmaceutically-acceptable carrier and also compositions in which a compound according to the invention (including RER (SEQ ID NO.:9)) is chemically or physically linked to a further molecule or vehicle to form a complex for pharmaceutical delivery of the compound.

The compound which is most preferred in the medical uses and pharmaceutical compositions is:

Arg-Glu-Arg (SEQ ID No:9)

which corresponds to amino acid residues 328-330 of human APP.

The invention further provides a compound having a formula comprising $X_1$-Ser-Met-Arg-Glu-Arg-$X_2$ (VII) (SEQ ID NO.:35)

wherein $X_1$ and $X_2$, which may be the same or different, each represents from zero to 30 amino acid residues, the amino acid residues of $X_1$ and $X_2$ being such that, when $X_1$ and $X_2$ are not both zero, the formula represents a reverse-order sequence corresponding to amino acid residues 332 to 328 of human APP and from zero to 30 successive amino acid residues of human APP extending in each direction therefrom, the formula also comprising sequences closely homologous to said reverse-order sequence and sequences in which said amino acids thereof are replaced by nonstandard amino acids and/or by derivatives of said amino acids, provided always that the compound is not Met-Val-Gln-Ser-Met-Arg-Glu-Arg-His- (SEQ ID No: 7)
Lys-Ala-Glu-Leu-Arg-Glu-Lys-Ala Subject to the above proviso, formula (VII) thus includes within its scope polypeptides which consist of a core sequence of the five amino acid residues 332 to 328 of human APP in reverse order relative to human APP and, extending therefrom in the N-terminal direction, up to 30 of amino acid residues 333 to 362 of human APP and, in the C-terminal direction, up to 30 of amino acid residues 327 to 328 of human APP, the whole forming a reverse-order sequence relative to human APP.

In formula (VII), $X_1$ is preferably from zero to 20 and/or $X_2$ is from zero to 20. More preferably, $X_1$ is from zero to 10 and/or $X_2$ is from zero to 10. Still more preferably, $X_1$ and/or $X_2$ is zero.

In other preferred compounds of formula (VII), $X_1$ is 2 or less and $X_2$ is 8 or less.

BRIEF DESCRIPTION OF THE DRAWINGS

The drawings of this specification consist of the following:

FIG. 1 which shows the amino acid sequence of human APP (SEQ ID NO.:1) and chick APP (SEQ ID NO.:2), as referred to hereinbefore;

DETAILED DESCRIPTION OF THE INVENTION

Figure 2:
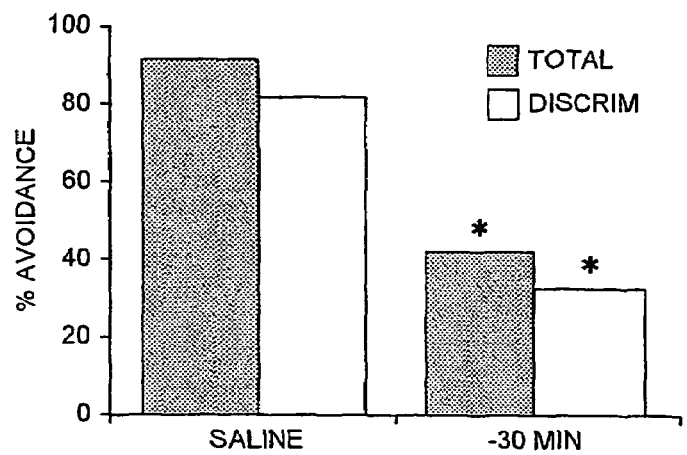
FIG. 2 shows the effect of β-amyloid 12-28 polypeptide on memory formation.

The invention will now be described further by way of example with reference to the following experimental procedures and results.

Materials and Methods

Animals and Training

Commercially obtained Ross Chunky eggs were incubated and hatched in brooders and held until 16±6 hours old. Chicks were placed in pairs in small aluminium pens. Following an equilibration period of an hour, the chicks were pretrained and trained essentially as described by Lossner and Rose (J. Neurochem. 41, 1357-1363 (1983), the contents of which are incorporated herein by reference). Pretraining involved three 10 s presentations of a small (2 mm diameter) white bead, at approximately 5 minute intervals. Chicks, which failed to peck the bead at least twice in three presentations (less than 5%), were not used subsequently, but remained in their pens for the duration of the experiment. Two training techniques were used: "strong" and "weak" training. In both, 5 to 10 minutes after the last pre-training trial, chicks were trained by a 10 s presentation of a 4 mm diameter chrome bead, which had been dipped in the bitter-tasting methylanthranilate. Control chicks pecked at a water-coated or dry bead. In the "strong" version of the task, 100% methylanthranilate was used. In the "weak" version, 10% methylanthranilate was used. Chicks spontaneously pecked at the training or control beads within 20 s. Chicks that peck at the bitter bead evinced a disgust reaction and would not normally peck at a similar, but dry bead for some hours subsequently. At various times following training chicks were tested, by offering them a dry 4 mm diameter chrome bead, followed 10 minutes later by a small (2 mm diameter) white bead, each for 20 to 30 s. Animals were tested by an experimenter blind as to which treatment each chick had received. Chicks are considered to remember the task if they avoid the chrome bead at test but peck at the white bead (discriminate), and to have forgotten it if they peck at both beads. Recall is calculated as a percent avoidance score (percentage of chicks which avoid the chrome bead) and as a discrimination score (percentage of chicks which avoid the chrome but peck at the white bead). The use of the discrimination score ensures that chicks can indeed see and peck accurately at the bead; and hence that the avoidance of the chrome bead is not due to non-specific factors such as lack of visuo-motor coordination, motivation, attention, arousal, etc. but is a positive act, demonstrating memory for the distasteful stimulus. Each chick was trained and tested only once and differences between groups tested for statistical significance by g-test described by Sokal and Rohlf (Biometry: the Principles and Practice of Statistics in Biological Research (2nd edition), W H Freeman, New York (1981)), the contents of which are incorporated herein by reference. The validity of this particular training task used to assess memory formation is extensively discussed by Andrew (Neural and Behavioural Plasticity: the Use of the Domestic Chick as a Model, Oxford University Press, Oxford, UK (1991), the contents of which are incorporated herein by reference.

Chicks trained on the strong version of the task were found to recall the avoidance for at least 48 hours, and more than 80% were found normally to avoid and discriminate on test at 24 hours. Therefore if agents that are amnesic—that is, cause the chick not to remember—are administered, chicks will demonstrate forgetting by pecking rather than avoiding the chrome bead on test. By contrast, chicks were found normally to remember the "weak" version of the task for only a few hours—some 6 to 8 hours in all; retention at 24 hours was normally reduced to some 20 to 30%. Thus the learning experience is not committed to long-term memory. Agents that are memory enhancers can thus be tested. A memory enhancing agent, administered to a chick trained on the weak learning task, produces an increase in retention—increased avoidance of the chrome bead—at 24 hours. That is, such memory enhancers help convert weak to strong learning by enabling the transition from shorter to longer-term memory.

Peptide Injections

Bilateral intracranial injections (2 μg/hemisphere) of either saline, or solutions in saline of different peptides (0.5 to 5 μg/hemisphere) homologous to different regions of the external domain of human APP were injected intracerebrally into a specific brain region, known to be required for memory formation (the intermediate hyperstriatum ventrale) at different time-points pre- or post-training using a 5 μg Hamilton syringe fitted with a plastic sleeve to allow a penetration of 3 mm. After completion of the injection, the needle was kept in place for 5 s. Correct placement was ensured by using a specially designed headholder described by Davis et al (Physiol. Behav. 22, 177-184 (1979), the contents of which are incorporated herein by reference) and was routinely visually monitored postmortem. Peptides or other substances were administered at various times either before or after the training protocol. Chicks were tested at different time points post-training as described above. The general behaviour of the chicks following injections was observed to detect any potential non-specific or adverse reactions to the injections.

Peptide Materials

The polypeptides administered were synthesised using a conventional peptide synthesiser in a manner which is well-known to those skilled in the art. The synthesised polypeptides were purified by use of RP-HPLC and purity further checked by mass spectrometry (MALDI-TOF), both techniques being well known to those skilled in the art. The polypeptides after synthesis were kept under argon in a lyophilised state, the argon preventing oxidation of cysteine, methionine and tryptophan in particular.

Polypeptide synthesis as just mentioned is carried out by MWG-Biotech UK Limited of Milton Keynes, UK.

RERMS (SEQ ID NO.:3) is also available from Bachem Limited of St. Helens, Merseyside, UK.

Ac-RER can be synthesised by techniques well-known to those skilled in the art. It was obtained from Cambridge Research Biochemicals Limited of Billingham, Cleveland, UK.

For further details regarding synthetic methods for the preparation of peptides and peptide derivatives, reference is made to "Principles of Peptide Synthesis" by M. Bodanszky, 2nd Edition (Springer Laboratory, 1993), the entire contents of which are incorporated herein by reference.

EXPERIMENTAL RESULTS

It is well known in many animal model systems for the study of memory that injection of β-amyloid and β-amyloid peptides, such as β-amyloid 12-28, results in a failure of animals to retain recently acquired memories. FIG. 2 shows this result for a chick; injection of β-amyloid 12-28 into the brain 30 minutes prior to training chicks on the passive avoidance task results in amnesia in animals tested 30 minutes subsequently.

FIG. 2 shows in the left-hand half the percent avoidance measured in terms of total avoidance and discrimination for a saline control and in the right-hand half the percent avoidance measured when β-amyloid 12-28 is injected as described above 30 minutes pretraining and memory is tested 30 minutes posttraining.

Figure 3:
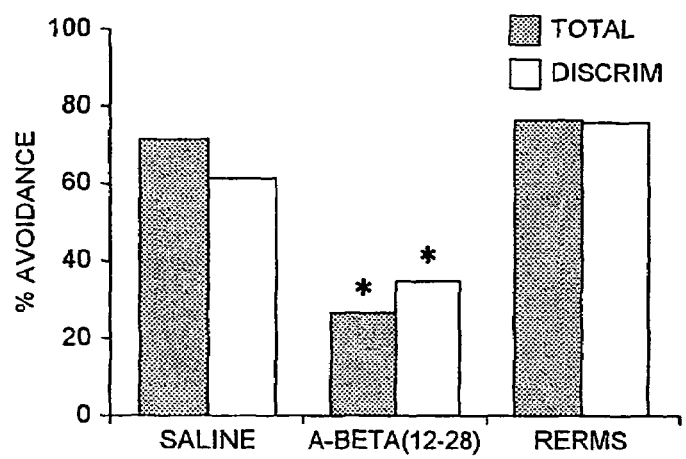
FIG. 3 shows the effect of RERMS (SEQ ID NO.:3) on β-amyloid 12-28 induced amnesia.

However, if amnesia is induced by injection of β-amyloid 12-28 30 minutes pretraining, and RERMS (SEQ ID NO.:3) is injected 20 minutes pretraining, memory retention is restored. FIG. 3 shows that in this case memory is normal at 24 hours post-training.

FIG. 3 shows on the left the percent avoidance measured in terms of total avoidance and discrimination for a saline control, in the centre the corresponding results when β-amyloid 12-28 is injected 30 minutes pretraining and memory tested 24 hours posttraining, and on the right the results when the pretraining injection of β-amyloid 12-28 is followed 10 minutes later by RERMS (SEQ ID NO.:3) and memory is again tested 24 hours posttraining.

It is thus shown that RERMS (SEQ ID NO.:3) can prevent the memory loss produced by β-amyloid 12-28, a component of the amyloid plaques characteristic of Alzheimer's disease.

It is known that disrupting the normal function of APP by blocking its external domain with a specific monoclonal antibody (mb22C11) around the time of training, whilst without effect on the ability of chicks to learn the passive avoidance response, prevents the transition to long term memory. The monoclonal antibody mb22C11, available from Boehringer-Mannheim, specifically recognises an epitope consisting of part of the external domain of APP.

Figure 4:
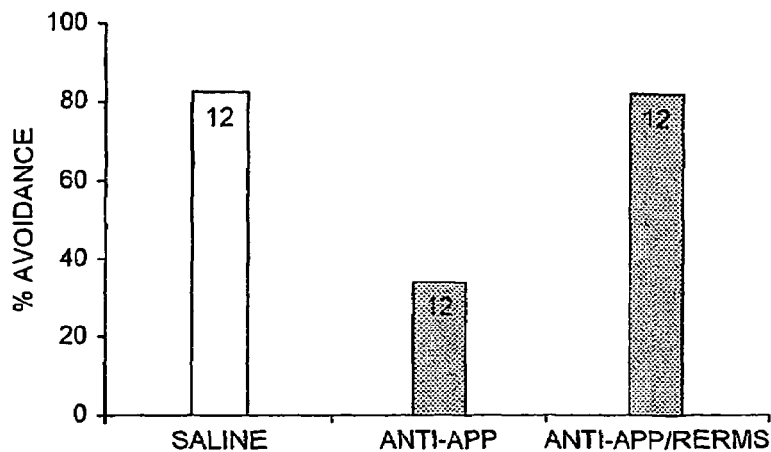
FIG. 4 shows the effect of RERMS (SEQ ID NO.:3) on anti-APP induced amnesia.

FIG. 4 shows on the left the percent avoidance measured for chicks injected with a saline control, in the centre the percent avoidance measured when mb22C11 is injected (1-5 µg in 2 µl) intracerebrally as described hereinbefore for peptide injections 30 minutes pretraining and, on the right, the percent avoidance measured when RERMS (SEQ ID NO.:3) is also injected 25 minutes after mb22C11 (5 minutes pretraining). In all cases, memory was tested 24 hours posttraining.

The results shown in FIG. 4 demonstrate that RERMS (SEQ ID NO.:3) injected 5 minutes before training will prevent antibody induced memory loss and that the peptide RERMS (SEQ ID NO.:3) can prevent anti-APP induced memory loss. Thus, RERMS (SEQ ID NO.:3) can prevent the memory loss resulting from disrupting the normal function of APP.

Figure 5A:
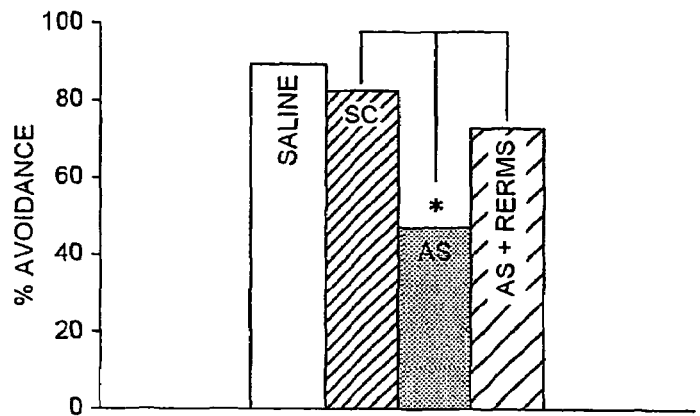
FIG. 5 shows the effect of RERMS (SEQ ID NO.:3), SMRER (SEQ ID NO.:4) and RSAER (SEQ ID NO.:5) on APP-antisense induced amnesia.
Figure 5B:
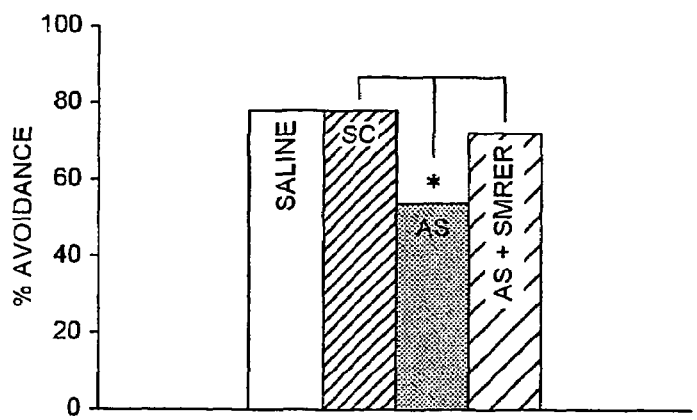
Figure 5C:
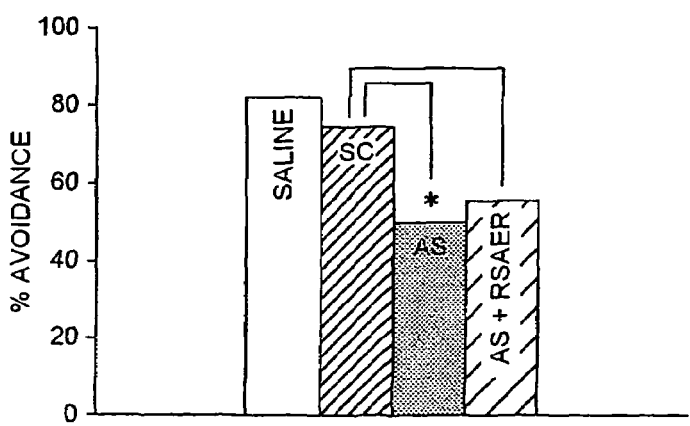
Figure 6:
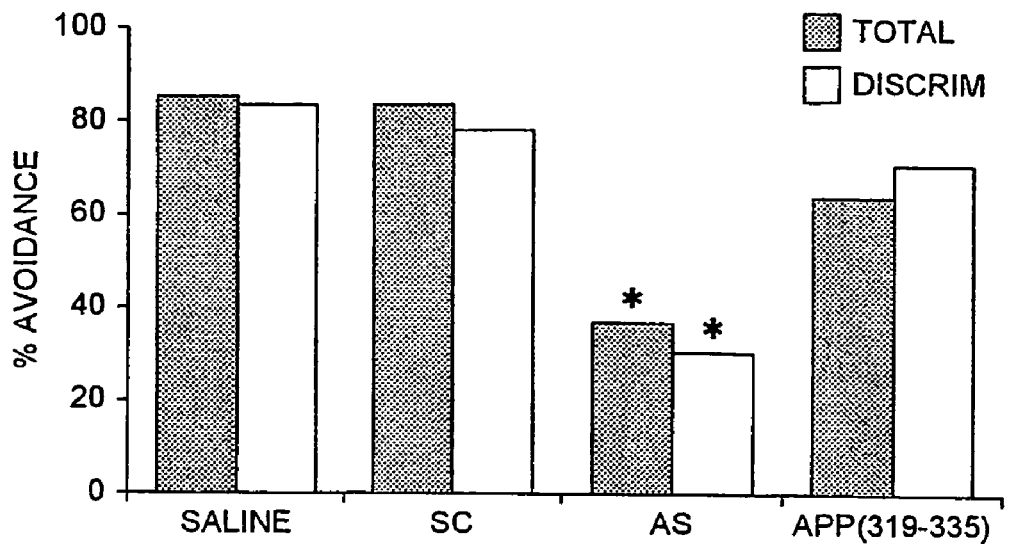
FIG. 6 shows the effect of APP 319-335 on APP-antisense induced amnesia.

FIGS. 5 and 6 show the effect of inducing memory loss by injection of a 16-mer end-protected phosphodiester oligodeoxynucleotide designed to correspond to the transcription start sites 146 and AUG1786 of the APP mRNA, immediately upstream of a ribozyme binding site. The oligodeoxynucleotide, 5'-CCC GAG GAC TGA GCC A-3' (SEQ ID No: 21) was further modified on the 2nd and 13th nucleotides to prevent internal looping and is available from King's College Molecular Medicine Unit, London, UK. The oligodeoxynucleotide was used in scrambled (SC) and antisense (AS) forms and administered as described hereinbefore for peptide administration in an amount of 0.6 to 1.0 µg in 2 µl.

In a first experiment, chicks were injected with saline, RERMS (SEQ ID NO.:3), SMRER (SEQ ID NO.:4) and RSAER (SEQ ID NO.:5) in various combinations in the amounts stated hereinbefore.

The results are shown in FIG. 5 which shows the percent avoidances measured on the "strong" learning task described hereinbefore. FIG. 5a shows the effect compared with a saline control of administration separately of SC oligodeoxynucleotide 12 hours pretraining and AS oligodeoxynucleotide 12 hours pretraining, together with the effect of administration of RERMS (SEQ ID NO.:3) following the AS oligodeoxynucleotide 30 minutes pretraining.

FIG. 5a shows that the SC oligodeoxynucleotide had no effect on memory but the AS compound had a significant effect of memory loss which was avoided to a substantial extent when RERMS (SEQ ID NO.:3) was administered.

FIG. 5b shows that similar results were obtained with the reverse-order pentapeptide SMRER (SEQ ID NO.:4).

FIG. 5c shows that the effect obtained with RERMS (SEQ ID NO.:3) and SMRER (SEQ ID NO.:4) is absent with the pentapeptide RSAER (SEQ ID NO.:5).

In a second experiment, SC and AS oligodeoxynucleotides were administered 12 hours pretraining. A polypeptide (APP 319-335) corresponding to amino acid residues 319 to 335 of human APP was injected 30 minutes pretraining. Chicks were tested for memory according to the "strong" version of the test described hereinbefore 30 minutes posttraining.

FIG. 6 shows successively from the left: the percent avoidance measured for a saline control; the percent avoidance measured when SC oligodeoxynucleotide was administered; the percent avoidance measured when AS oligodeoxynucleotide was administered; and the percent avoidance measured when APP 319-335 was administered 30 minutes pretraining following administration of AS oligodeoxynucleotide 12 hours pretraining. Each result is shown both in terms of total avoidance (left-hand column) and discrimination (right-hand column).

The results shown in FIG. 6 demonstrate that APP319-335 can prevent antisense induced memory loss.

Figure 7:
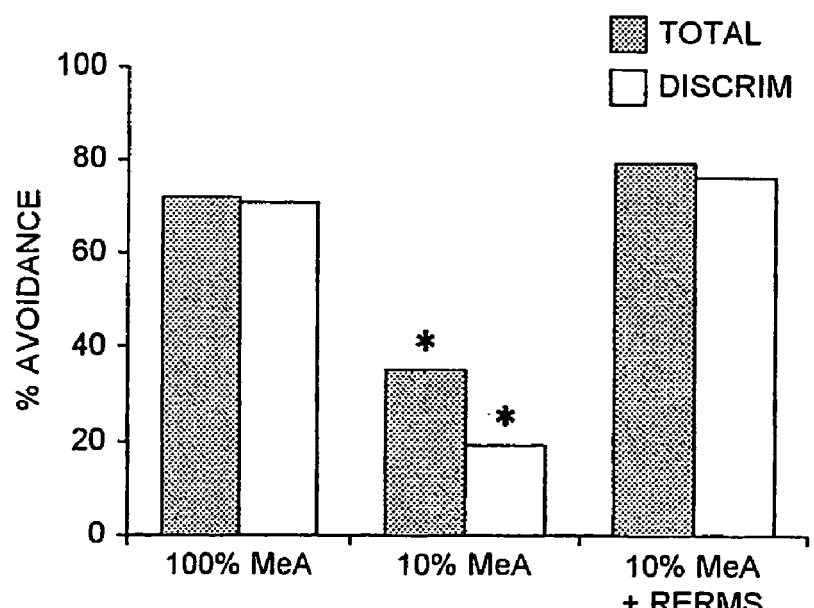
FIG. 7 shows the effect of RERMS (SEQ ID NO.:3) on weak training.
Figure 8:
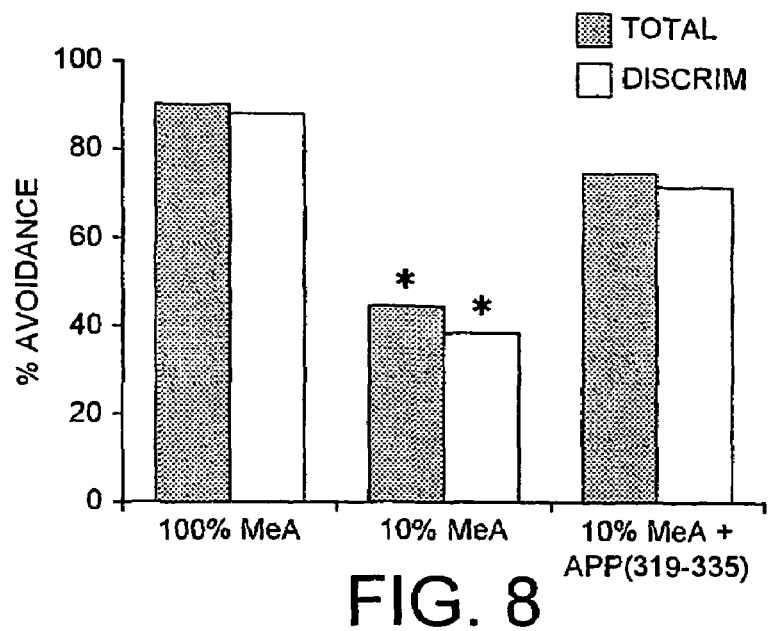
FIG. 8 shows the effect of APP 319-335 on weak training.

FIGS. 7 and 8 show the effects of RERMS (SEQ ID NO.:3) and APP 319-335 on memory in chicks trained on the "weak" memory test described hereinbefore.

As stated hereinbefore, weakly trained chicks (trained on 10% methylanthranilate) retain memory for the avoidance for only some 6 hours, and thereafter forget. FIG. 7 shows, on the left, the percent avoidance results (in terms of total avoidance and discrimination) for chicks trained on the "strong" version of the training, in the centre the corresponding results for "weak" training and, on the right, the effect of administration of RERMS (SEQ ID NO.:3) following "weak" training. The chicks were tested for memory 24 hours posttraining; RERMS (SEQ ID NO.:3) was administered in accordance with the procedure described hereinbefore 30 minutes pretraining.

FIG. 8 shows the corresponding results obtained when the APP 319-335 polypeptide was used instead of RERMS (SEQ ID NO.:3).

FIGS. 7 and 8 show that RERMS (SEQ ID NO.:3) and APP 319-335 if injected prior to training chicks on the weak task, enhance memory at 24 hours. They thus function as cognitive enhancers (nootropic agents). Thus, RERMS (SEQ ID NO.: 3) and APP 319-335 both enhance normal memory in weakly trained animals.

Figure 9:
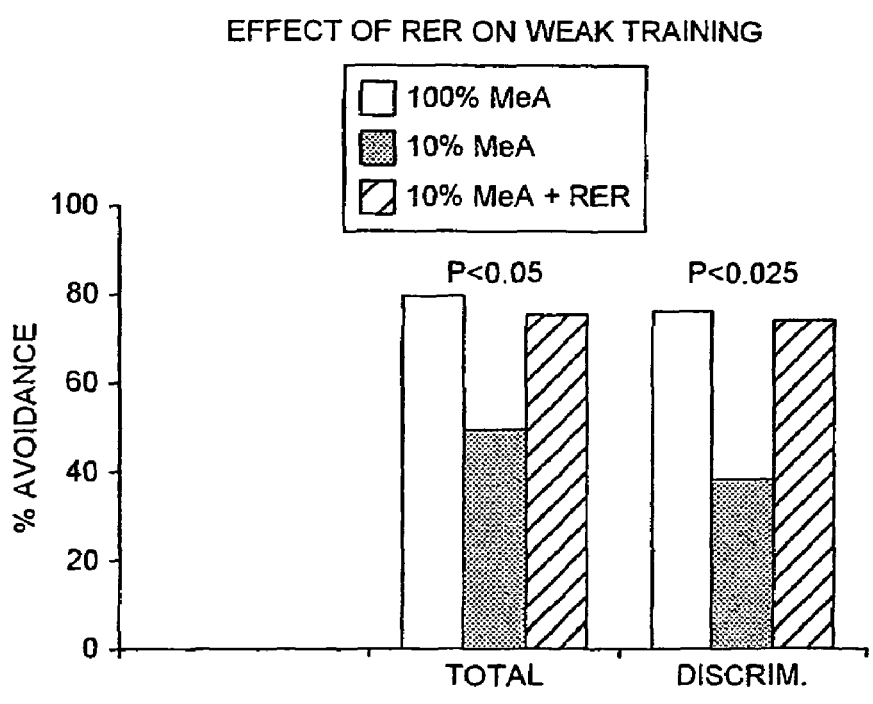
FIG. 9 shows the effect of RER (SEQ ID NO.:9) on weak training.

FIG. 9 shows the effect of RER (SEQ ID NO.:9) on memory in chicks trained on the "weak" memory test described hereinbefore.

As stated hereinbefore, weakly trained chicks (trained on 10% methylanthranilate) retain memory for the avoidance for only some 6 hours, and thereafter forget.

FIG. 9 shows, in the three columns on the left, on the left the percent avoidance results (in terms of total avoidance) for chicks trained on the "strong" version of the training, in the centre the corresponding results for "weak" training and, on the right, the effect of administration of RER (SEQ ID NO.:9) following "weak" training. The chicks were tested for memory 24 hours posttraining; RER (SEQ ID NO.:9) was administered in accordance with the procedure described hereinbefore 30 minutes pretraining.

FIG. 9 shows, on the right, the corresponding data in terms of discrimination.

FIG. 9 shows that RER (SEQ ID NO.:9), if injected prior to training chicks on the weak task, enhances memory at 24 hours. It thus functions as a cognitive enhancer (nootropic agent). Thus, RER (SEQ ID NO.:9) enhances normal memory in weakly trained animals.

Figure 10:
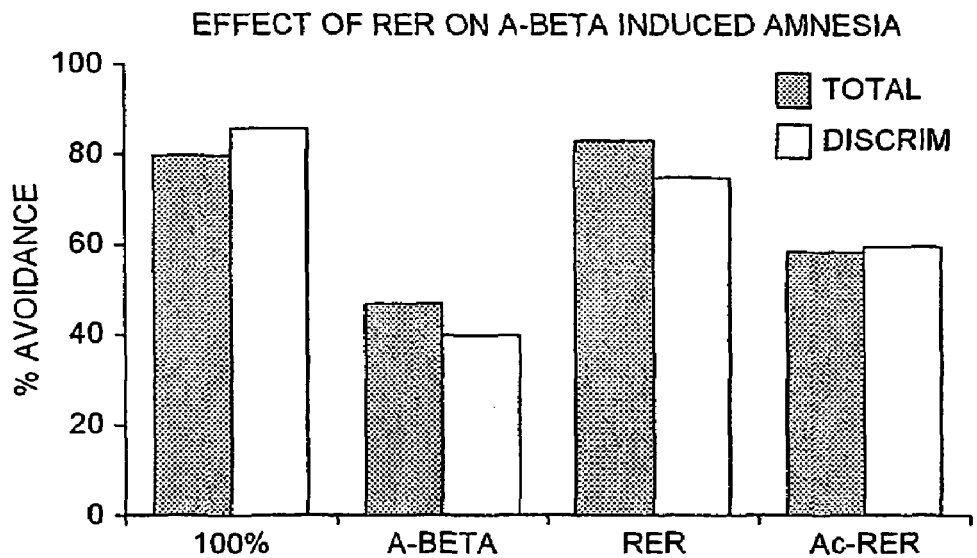
FIG. 10 shows the effects of RER (SEQ ID NO.:9) and Ac-RER on β-amyloid 12-28 induced amnesia.

FIG. 10 shows the effect of RER (SEQ ID NO.:9) and Ac-RER on β-amyloid 12-28 induced amnesia in chicks trained on the "strong" memory test described hereinbefore.

FIG. 10 shows from left to right the percent avoidance measured in terms of total avoidance and discrimination for
 chicks trained on the "strong" version of the training;
 the amnesic effect of β-amyloid 12-28 administered at 2 μg/hemisphere 30 mins prior to training;
 the effect of RER (SEQ ID NO.:9) administered at 2 μg/hemisphere 20 mins prior to training after administration of β-amyloid 12-28 30 mins prior to training; and
 the effect of Ac-RER administered at 2 μg/hemisphere 20 mins prior to training after administration of β-amyloid 12-28 30 mins prior to training.

The results in FIG. 10 show that both RER (SEQ ID NO.:9) and AC-RER have the effect of restoring memory measured 20 mins after administration of RER (SEQ ID NO.:9) or AC-RER, following amnesia induced by administration of β-amyloid 12-28.

The results also show that the memory-restorative effect of Ac-RER is less than that of RER (SEQ ID NO.:9) but indicate that Ac-RER is more stable after administration and therefore more suitable for peripheral administration.

Figure 11:
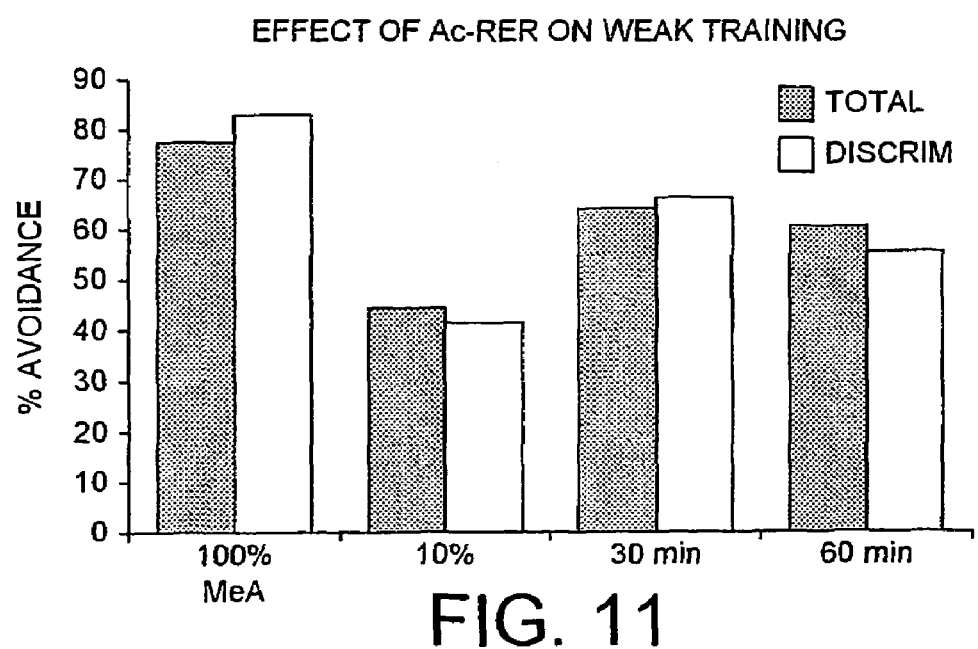
FIG. 11 shows the effect of Ac-RER on weak training.

FIG. 11 shows the effect of Ac-RER on memory in chicks trained on the "weak" memory test described hereinbefore.

FIG. 11 shows from left to right the percent avoidance measured in terms of total avoidance and discrimination for
 chicks trained on the "strong" version of the training:
 chicks trained on the "weak" version of the training;
 chicks trained on the "weak" version of the training after having had Ac-RER administered at 2 μg/hemisphere 30 mins beforehand; and
 chicks trained on the "weak" version of the training after having had Ac-RER administered at 2 μg/hemisphere 60 mins beforehand.

The results in FIG. 11 show that Ac-RER has the effect of improving the memory of weakly trained chicks when administered 30 or 60 minutes beforehand. The results also show that the effect 60 minutes after administration is still significant, although less than 30 minutes after administration.

The results therefore show that Ac-RER has the effect of a cognitive enhancer and that the effect is apparent over a significant time period.

Figure 12:
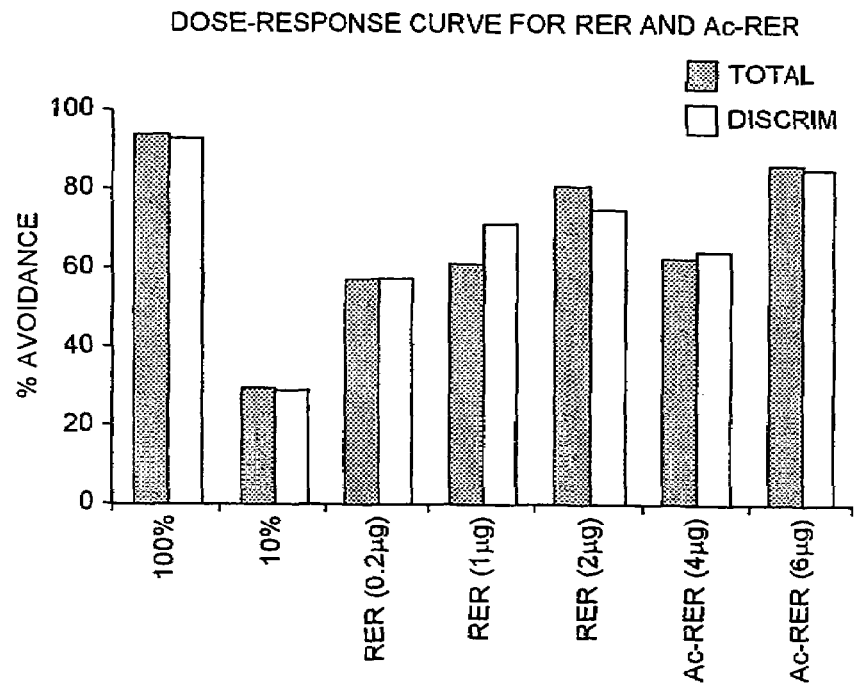
FIG. 12 shows the effects of differing doses of RER (SEQ ID NO.:9) and Ac-RER.

FIG. 12 shows the effect of different doses of RER (SEQ ID NO.:9) and AC-RER on memory in chicks trained on the "weak" memory test described hereinbefore.

FIG. 12 shows from left to right the percent avoidance measured in terms of total avoidance and discrimination for
 chicks trained on the "strong" version of the training;
 chicks trained on the "weak" version of the training;
 chicks trained on the "weak" version of the training after having had RER (SEQ ID NO.:9) administered 30 mins beforehand at 0.2 μg/hemisphere;
 chicks trained on the "weak" version of the training after having had RER (SEQ ID NO.:9) administered 30 mins beforehand at 1.0 μg/hemisphere;
 chicks trained on the "weak" version of the training after having had RER (SEQ ID NO.:9) administered 30 mins beforehand at 2.0 μg/hemisphere;
 chicks trained on the "weak" version of the training after having had Ac-RER administered 30 mins beforehand at 4.0 μg/hemisphere; and
 chicks trained on the "weak" version of the training after having had Ac-RER administered 30 mins beforehand at 6.0 μg/hemisphere.

The results in FIG. 12 show that both RER (SEQ ID NO.:9) and Ac-RER have the effect of improving the memory of weakly-trained chicks when administered 30 minutes beforehand and that higher doses of Ac-RER than of RER (SEQ ID NO.:9) are required to obtain a comparable effect.

The results therefore show that increased amounts of Ac-RER, in comparison to RER (SEQ ID NO.:9), are required to be used as a cognitive enhancer. This again indicates that Ac-RER is more stable after administration than RER (SEQ ID NO.:9) and therefore more suitable for peripheral administration.

Figure 13:
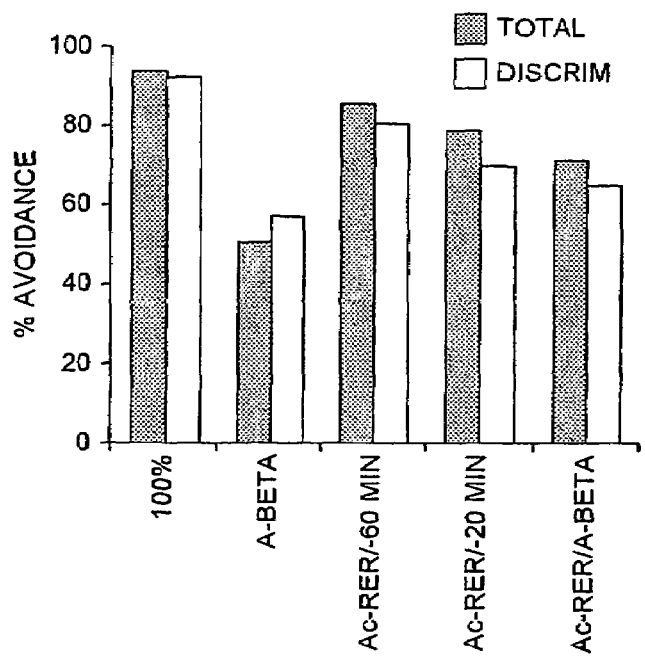
FIG. 13 shows the effect of Ac-RER on β-amyloid 12-28 induced amnesia.

FIG. 13 shows the effect of Ac-RER administered at different times on β-amyloid 12-28 induced amnesia in chicks trained on the "strong" memory test described hereinbefore.

FIG. 13 shows from left to right the percent avoidance measured in terms of total avoidance and discrimination for
 chicks trained on the "strong" version of the training;
 the amnesic effect of β-amyloid 12-28 administered at 2 μg/hemisphere 30 mins prior to training;
 the memory-restorative effect of Ac-RER administered at 4 μg/hemisphere 60 mins prior to training and 30 mins prior to administration of β-amyloid 12-28 at 2 μg/hemisphere;
 the memory-restorative effect of Ac-RER administered at 4 μg/hemisphere 20 mins prior to training and 10 mins after administration of β-amyloid 12-28 at 2 μg/hemisphere; and
 the memory-restorative effect of Ac-RER administered at 4 μg/hemisphere together with β-amyloid 12-28 at 2 μg/hemisphere 30 mins prior to training.

The results of FIG. 13 show that Ac-RER has the effect of restoring memory when amnesia has been induced by β-amyloid 12-28. The effect is manifested regardless of whether Ac-RER is administered before, after or simultaneously with the amnesia-inducing β-amyloid 12-28.

The role of APP in memory formation has been attributed to its involvement in cell-to-substrate adhesion processes. The data reported suggests that the APP involvement in memory formation most probably involves change in signal transduction events. The post-training time within which the antibody and antisense-induced amnesia, and within which RER (SEQ ID NO.:9), Ac-RER, RERMS (SEQ ID NO.:3) and SMRER (SEQ ID NO.:4) prevents amnesia, corresponds to that during which memory formation is vulnerable to disruption of the putative signal-transduction functions of APP.

The chick system is a good one for exploring these issues, because the learning task is precise and sharply timed, and permits one also to be sure that any observed effect of an injected substance is specific to retention and not either to acquisition or to concomitant processes such as visual acuity, arousal or motor activity. Further, the role of other cell adhesion molecules in the cascade leading to synaptic modulation has been well mapped, so that the effects of either blocking or attempting to rescue functional APP activity can be set into an established context: see Rose, Learn. Memory 7, 1-17 (2000) the contents of which are fully incorporated herein by reference.

It is therefore indicated by the experimental results reported above that compounds of the present invention are effective for the treatment and/or prevention of neurological diseases and disorders and as cognitive enhancers (nootropic agents) in other animals, including human and non-human mammals. The compounds are therefore effective in the treatment and/or prevention of Alzheimer's disease in humans and other neurodegenerative diseases and disorders in animals generally, including humans. Such animals include transgenic and other animal models for Alzheimer's disease.

As used herein, except where the context indicates otherwise, the terms "treatment", "treat" and analogous expressions used in relation to neurodegenerative diseases include within their scope not only treatment when symptoms are apparent but also the partial or total prevention of such diseases and delay in their onset in patients or animals who are subjected to treatment before onset of the disease or its symptoms become apparent.

The compounds of the present invention may be administered intracereballly as described above, or may be administered peripherally, for example intramuscularly, intravenously, transdermally or orally, preferably after complexation as described above. Instead or in addition, the compounds may be protected against alteration between administration and effectiveness, for example by addition of protective groups.

The experimental results of FIGS. 10 to 13 show that the polypeptide derivatives of the present invention, particularly Ac-RER, are effective for longer time periods after administration than their analogues lacking protective groups and are therefore particularly suitable for peripheral administration.

The compounds of the present invention may also be formulated as pharmaceutical compositions as referred to hereinbefore, particularly such compositions as are capable of crossing the blood-brain barrier and thereby be suitable for peripheral administration.

In all events a suitable dose of peptide compounds according to the invention is from 10 to 100 µg/kg body weight of the animal being treated.

As used herein, the term "effective to treat" in the context of a neurodegenerative disease means that amount of the compound(s) used in the treatment which causes a reduction or stabilisation or, as the case may be, prevents or delays the appearance of such symptoms as measured by standard medical or psychological criteria, for example as disclosed in Handbook of Memory Disorders (eds: A D Baddeley, B A Wilson and F N Watts), Wiley (1995), the disclosure of which is herein incorporated by reference.

As used herein, the term "effective to treat" in relation to a cognitive enhancement means an amount of the compound(s) used in the treatment which causes an improvement in cognitive power as measured by psychological criteria, for example as disclosed in Handbook of Memory Disorders (eds: A D Baddeley, B A Wilson and F N Watts), Wiley (1995), the disclosure of which is herein incorporated by reference.

SEQUENCE LISTING FREE TEXT

| SEQ ID NO. | Free Text <223> |
|---|---|
| 3 | Description of Artificial Sequence: 5-mer polypeptide |
| 4 | Description of Artificial Sequence: 5-mer polypeptide |
| 5 | Description of Artificial Sequence: 5-mer polypeptide |
| 6 | Description of Artificial Sequence: 17-mer polypeptide |
| 7 | Description of Artificial Sequence: 17-mer polypeptide |
| 8 | Description of Artificial Sequence: 17-mer polypeptide |
| 9 | Description of Artificial Sequence: 3-mer polypeptide |
| 10 | Description of Artificial Sequence: 4-mer polypeptide |
| 11 | Description of Artificial Sequence: 4-mer polypeptide |
| 12 | Description of Artificial Sequence: 16-mer polypeptide |
| 13 | Description of Artificial Sequence: 15-mer polypeptide |
| 14 | Description of Artificial Sequence: 14-mer polypeptide |
| 15 | Description of Artificial Sequence: 12-mer polypeptide |
| 16 | Description of Artificial Sequence: 11-mer polypeptide |
| 17 | Description of Artificial Sequence: 11-mer polypeptide |
| 18 | Description of Artificial Sequence: 10-mer polypeptide |
| 19 | Description of Artificial Sequence: 6-mer polypeptide |
| 20 | Description of Artificial Sequence: 22-mer polypeptide |
| 21 | Description of Artificial Sequence: end-protected 16-mer oligonucleotide modified at positions 2 & 13 to prevent internal looping |
| 22 | Description of Artificial Sequence: 40-mer polypeptide |

The invention claimed is:

1. A pharmaceutical composition comprising: (a) a peptide consisting of the following sequence of amino acids:

Arg-Glu-Arg (I)

wherein each amino acid residue is in the D-form or the L-form or in the form of a salt thereof, at least one functional group of the N-terminal arginine residue of said peptide being protected by at least one protective group, and (b) pharmaceutically acceptable carrier, filler, or excipient.

2. A composition according to claim 1, in which the protected functional group(s) comprise one or more amino groups.

3. A composition according to claim 2, in which at least one protected amino group is protected by replacement of only one of its hydrogen atoms by a protective group.

4. A composition according to claim 1, in which the protected functional group(s) comprise one or more carboxyl groups.

5. A composition according to claim 1, in which at least one protective group is an acyl group represented by the formula:

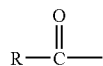

wherein R represents a substituted or unsubstituted straight- or branched-chain alkyl group, a substituted or unsubstituted cycloalkyl group, a substituted or unsubstituted straight or branched-chain aralkyl group or a substituted or unsubstituted aryl group, the groups R being the same or different when two or more are present.

6. A composition according to claim 5, in which R represents a $C_1$ to $C_6$ straight- or branched-chain alkyl group.

7. A composition according to claim 6, in which R represents a methyl group.

8. A pharmaceutical composition according to claim 1 wherein said N-terminal arginine residue of said peptide is protected by an acetyl group substituted for one of the hydrogen atoms of the N-terminal amino group of said N-terminal arginine residue.

9. A pharmaceutical composition comprising: (a) a compound having the formula:

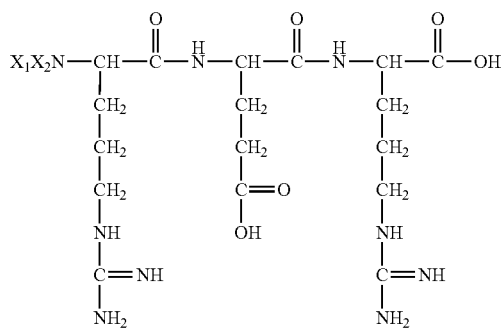

in which $X_1$ is a protective group and $X_2$ is H or a protective group, and (b) a pharmaceutically acceptable carrier, filler, or excipient.

10. A pharmaceutical composition comprising: (a) a compound having the formula

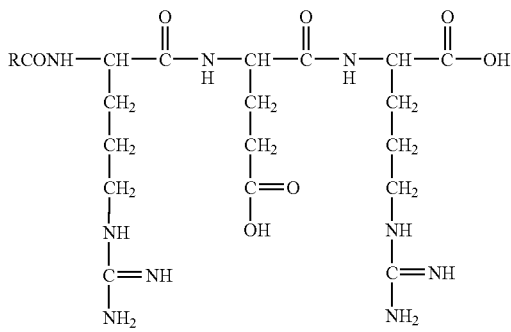

in which R represents a substituted or unsubstituted straight- or branched-chain alkyl group, a substituted or unsubstituted cycloalkyl group, a substituted or unsubstituted straight or branched-chain aralkyl group or a substituted or unsubstituted aryl group, and (b) a pharmaceutically acceptable carrier, filler, or excipient.

11. A composition according to claim 9, in which R represents a $C_1$ to $C_6$ straight- or branched-chain alkyl group.

12. A pharmaceutical composition comprising: (a) a compound having the formula

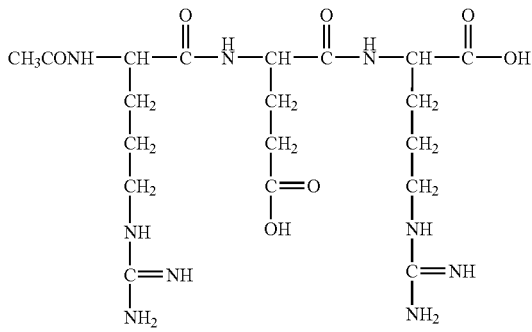

and (b) a pharmaceutically-acceptable carrier, filler, or excipient.

13. A pharmaceutical composition comprising:

(a) a peptide consisting of the following sequence of amino acids:

Arg-Glu-Arg (I)

wherein each amino acid residue is in the D-form or the L-form or in the from of a salt thereof, at least one functional group of the N-terminal arginine residue of said peptide being protected by at least one protective group, said peptide being chemically or physically linked to a further molecule or vehicle for pharmaceutical delivery, and (b) a pharmaceutically acceptable carrier, filler, or excipient.

14. A pharmaceutical composition according to claim 13, wherein said N-terminal arginine residue of said peptide is protected by an acetyl group substituted for one of the hydrogen atoms of the N-terminal amino group of said N-terminal arginine residue.

15. A pharmaceutical composition comprising: (a) a peptide consisting of either of the following amino acid sequences:

```
Met-Arg-Glu-Arg                    (SEQ ID NO 11)
Ser-Met-Arg-Glu-Arg                (SEQ ID NO 4)
``` wherein each amino acid residue is independently in the D-form or the L-form, or in the form of a salt thereof, and (b) a pharmaceutically-acceptable carrier, filler, or excipient.

16. A pharmaceutical composition in which a peptide consisting of any of the following amino acid sequences:

```
Arg-Glu-Arg                        (SEQ ID NO 9)
Arg-Glu-Arg-Met                    (SEQ ID NO 10)
Met-Arg-Glu-Arg                    (SEQ ID NO 11)
Ser-Met-Arg-Glu-Arg                (SEQ ID NO 4)
``` wherein each amino acid residue is independently in the D-form or the L-form, or in the form of a salt thereof, is chemically or physically linked to a further molecule or vehicle to form a complex for pharmaceutical delivery of said compound.

17. A pharmaceutical composition comprising: (a) a peptide consisting of either of the following amino acid sequences:

```
Arg-Glu-Arg                        (SEQ ID NO 9)
Arg-Glu-Arg-Met                    (SEQ ID NO 10)
``` wherein each amino acid residue is independently in the D-form or the L-form, or in the form of a salt thereof, and (b) a pharmaceutically-acceptable carrier, filler, or excipient.

* * * * *

UNITED STATES PATENT AND TRADEMARK OFFICE
CERTIFICATE OF CORRECTION

PATENT NO.         : 7,622,446 B2
APPLICATION NO.    : 10/475281
DATED              : November 24, 2009
INVENTOR(S)        : Radmila Mileusnic et al.

It is certified that error appears in the above-identified patent and that said Letters Patent is hereby corrected as shown below:

The title page, item (63), "Continuation" should read --Continuation-in-part--.
Column 3, line 65, each occurrence of "Saito" should read --Saitoh--; in line 66, "Neuobiol." should read --Neurobiol.--.
Column 5, line 1, "Multhorp" should read --Multhaup--.
Column 8, the formula at lines 1-15 should read:

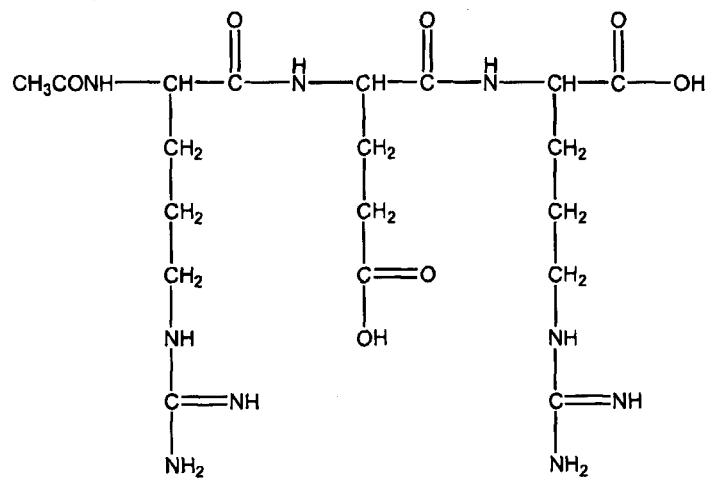

Column 11, lines 28, 30 and 58, each occurrence of "AC" should read --Ac--.
Column 38, line 23, "9" should read --10--.
Column 40, line 4, delete "to form a complex".

Signed and Sealed this

Eighteenth Day of May, 2010

David J. Kappos
*Director of the United States Patent and Trademark Office*

SEQUENCE LISTING

```
<160> NUMBER OF SEQ ID NOS: 22

<210> SEQ ID NO 1
<211> LENGTH: 695
<212> TYPE: PRT
<213> ORGANISM: Homo sapiens

<400> SEQUENCE: 1

Met Leu Pro Gly Leu Ala Leu Leu Leu Leu Ala Ala Trp Thr Ala Arg
 1               5                   10                  15
```

```
Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
            405                 410                 415

Asn Met Leu Lys Lys Tyr Val Arg Ala Glu Gln Lys Asp Arg Gln His
        420                 425                 430
```

```
Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
690                 695

<210> SEQ ID NO 2
<211> LENGTH: 534
<212> TYPE: PRT
<213> ORGANISM: Chick

<400> SEQUENCE: 2

Gly Met Asn Leu His Asp Tyr Gly Met Leu Leu Pro Cys Gly Ile Asp
1               5                   10                  15

Lys Phe Arg Gly Val Glu Phe Val Cys Cys Pro Leu Ala Glu Glu Ser
                20                  25                  30

Asp Asn Leu Asp Ser Ala Asp Ala Glu Asp Asp Ser Asp Val Trp
            35                  40                  45

Trp Gly Gly Ala Asp Ala Asp Tyr Ala Asp Gly Ser Asp Asp Lys Val
        50                  55                  60

Val Glu Glu Gln Pro Glu Glu Asp Glu Leu Thr Val Val Glu Asp
65                  70                  75                  80

Glu Asp Ala Asp Asp Asp Asp Asp Asp Gly Asp Glu Ile Glu Glu
                85                  90                  95

Thr Glu Glu Glu Tyr Glu Ala Thr Glu Arg Thr Thr Ser Ile Ala
            100                 105                 110
```

-continued

Thr Thr Thr Thr Thr Thr Thr Glu Ser Val Glu Val Val Arg Val
            115                 120                 125

Pro Thr Thr Ala Ala Ser Thr Pro Asp Ala Val Asp Lys Tyr Leu Glu
    130                 135                 140

Thr Pro Gly Asp Glu Asn Glu His Ala His Phe Gln Lys Ala Lys Glu
145                 150                 155                 160

Arg Leu Glu Ala Lys His Arg Glu Arg Met Ser Gln Val Met Arg Glu
                165                 170                 175

Trp Glu Glu Ala Glu Arg Gln Ala Lys Asn Leu Pro Lys Ala Asp Lys
            180                 185                 190

Lys Ala Val Ile Gln His Phe Gln Glu Lys Val Glu Ser Leu Glu Gln
        195                 200                 205

Glu Ala Ala Asn Glu Arg Gln Gln Leu Val Glu Thr His Met Ala Arg
    210                 215                 220

Val Glu Ala Met Leu Asn Asp Arg Arg Ile Ala Leu Glu Asn Tyr
225                 230                 235                 240

Ile Thr Ala Leu Gln Thr Val Pro Pro Arg Pro Arg His Val Phe Asn
                245                 250                 255

Met Leu Lys Lys Tyr Val Arg Ala Glu Gln Lys Asp Arg Gln His Thr
            260                 265                 270

Leu Lys His Phe Glu His Val Arg Met Val Asp Pro Lys Lys Ala Ala
        275                 280                 285

Gln Ile Arg Ser Gln Val Met Thr His Leu Arg Val Ile Tyr Glu Arg
    290                 295                 300

Met Asn Gln Ser Leu Ser Phe Leu Tyr Asn Val Pro Ala Val Ala Glu
305                 310                 315                 320

Glu Ile Gln Asp Glu Val Asp Glu Leu Leu Gln Lys Glu Gln Asn Tyr
                325                 330                 335

Ser Asp Asp Val Leu Ala Asn Met Ile Ser Glu Pro Arg Ile Ser Tyr
            340                 345                 350

Gly Asn Asp Ala Leu Met Pro Ser Leu Thr Glu Thr Lys Thr Thr Val
        355                 360                 365

Glu Leu Leu Pro Val Asp Gly Glu Phe Ser Leu Asp Asp Leu Gln Pro
    370                 375                 380

Trp His Pro Phe Gly Val Asp Ser Val Pro Ala Asn Thr Glu Asn Glu
385                 390                 395                 400

Val Glu Pro Val Asp Ala Arg Pro Ala Ala Asp Arg Gly Leu Thr Thr
                405                 410                 415

Arg Pro Gly Ser Gly Leu Thr Asn Val Lys Thr Glu Glu Val Ser Glu
            420                 425                 430

Val Lys Met Asp Ala Glu Phe Arg His Asp Ser Gly Tyr Glu Val His
        435                 440                 445

His Gln Lys Leu Val Phe Phe Ala Glu Asp Val Gly Ser Asn Lys Gly
    450                 455                 460

Ala Ile Ile Gly Leu Met Val Gly Gly Val Val Ile Ala Thr Val Ile
465                 470                 475                 480

Val Ile Thr Leu Val Met Leu Lys Lys Lys Gln Tyr Thr Ser Ile His
                485                 490                 495

His Gly Val Val Glu Val Asp Ala Ala Val Thr Pro Glu Glu Arg His
            500                 505                 510

Leu Ser Lys Met Gln Gln Asn Gly Tyr Glu Asn Pro Thr Tyr Lys Phe
        515                 520                 525

Phe Glu Gln Met Gln Asn
    530

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: 5-mer
      polypeptide

<400> SEQUENCE: 3

Arg Glu Arg Met Ser
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: 5-mer
      polypeptide

<400> SEQUENCE: 4

Ser Met Arg Glu Arg
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: 5-mer
      polypeptide

<400> SEQUENCE: 5

Arg Ser Ala Glu Arg
  1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: 17-mer
      polypeptide

<400> SEQUENCE: 6

Ala Lys Glu Arg Leu Glu Ala Lys His Arg Glu Arg Met Ser Gln Val
  1               5                  10                  15

Met

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: 17-mer
      polypeptide

<400> SEQUENCE: 7

Met Val Gln Ser Met Arg Glu Arg His Lys Ala Glu Leu Arg Glu Lys
  1               5                  10                  15

Ala

<210> SEQ ID NO 8

```
<211> LENGTH: 17
<212> TYPE: PRT
<213> ORGANISM: Artificial Sequence
<220> FEATURE:
<223> OTHER INFORMATION: Description of Artificial Sequence: 17-mer
      polypeptide

<400> SEQUENCE: 8

Val His His Gln Lys Leu Val Phe Phe Ala Glu Asp Val Gly Ser Asn
 1               5                  10                  15

Lys

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: 3-mer
                        polypeptide

<400> SEQUENCE: 9

Arg Glu Arg
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: 4-mer
                        polypeptide

<400> SEQUENCE: 10

Arg Glu Arg Met
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: 4-mer
                        polypeptide

<400> SEQUENCE: 11

Met Arg Glu Arg
 1

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: 16-mer
                        polypeptide

<400> SEQUENCE: 12

Gln Lys Ala Lys Glu Arg Leu Glu Ala Lys His Arg Glu Arg Met Ser
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: 15-mer
                        polypeptide
```

```
<400> SEQUENCE: 13

Glu Arg Leu Glu Ala Lys His Arg Glu Arg Met Ser Gln Val Met
 1               5                  10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: 14-mer
                        polypeptide

<400> SEQUENCE: 14

Ala Lys Glu Arg Leu Glu Ala Lys His Arg Glu Arg Met Ser
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: 12-mer
                        polypeptide

<400> SEQUENCE: 15

Glu Arg Leu Glu Ala Lys His Arg Glu Arg Met Ser
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: 11-mer
                        polypeptide

<400> SEQUENCE: 16

Glu Arg Leu Glu Ala Lys His Arg Glu Arg Met
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: 11-mer
                        polypeptide

<400> SEQUENCE: 17

Ala Lys His Arg Glu Arg Met Ser Gln Val Met
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: 10-mer
                        polypeptide

<400> SEQUENCE: 18

Glu Arg Leu Glu Ala Lys His Arg Glu Arg
 1               5                  10

<210> SEQ ID NO 19
<211> LENGTH: 6
<212> TYPE: PRT
```

```
<213> ORGANISM: Artificial Sequence
<220> FEATURE:
<223> OTHER INFORMATION: Description of Artificial Sequence: 6-mer
                        polypeptide

<400> SEQUENCE: 19

His Arg Glu Arg Met Ser
  1               5

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: 22-mer
                        polypeptide

<400> SEQUENCE: 20

Phe Gln Lys Ala Lys Glu Arg Leu Glu Ala Lys His Arg Glu Arg Met
  1               5                  10                  15

Ser Gln Val Met Arg Glu
            20

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: end-
                        protected 16-mer oligodeoxynucleotide modified
                        at positions 2 & 13 to prevent internal looping

<400> SEQUENCE: 21
cccgaggact gagcca                                                       16

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: 40-mer
                        polypeptide

<400> SEQUENCE: 22

Thr Pro Asp Ala Val Asp Lys Tyr Leu Glu Thr Pro Gly Asp Glu Asn
  1               5                  10                  15

Glu His Ala His Phe Gln Lys Ala Lys Glu Arg Leu Glu Ala Lys His
                 20                  25                  30

Arg Glu Arg Met Ser Gln Val Met
            35                  40
```